(12) United States Patent
Ruan

(10) Patent No.: US 11,912,716 B2
(45) Date of Patent: Feb. 27, 2024

(54) COMPOUND, PREPARATION METHOD AND USE THEREOF

(71) Applicant: GUANGXI JIUFU BIOTECHNOLOGY CO., LTD, Guangxi (CN)

(72) Inventor: Jun Ruan, Guangxi (CN)

(73) Assignee: GUANGXI JIUFU BIOTECHNOLOGY CO., LTD, Nanning (CN)

( * ) Notice: Subject to any disclaimer, the term of this patent is extended or adjusted under 35 U.S.C. 154(b) by 557 days.

(21) Appl. No.: 17/195,624

(22) Filed: Mar. 8, 2021

(65) Prior Publication Data
US 2021/0188865 A1    Jun. 24, 2021

Related U.S. Application Data

(63) Continuation-in-part of application No. PCT/CN2019/111538, filed on Oct. 16, 2019.

(30) Foreign Application Priority Data

Dec. 5, 2018  (CN) .......................... 201811482596.8

(51) Int. Cl.
*C07D 493/18*    (2006.01)
*A61P 25/36*    (2006.01)

(52) U.S. Cl.
CPC ............ *C07D 493/18* (2013.01); *A61P 25/36* (2018.01)

(58) Field of Classification Search
CPC ..... C07D 493/18; C07D 493/08; A61P 25/36; A61P 25/30; Y02P 20/54; A23L 33/10; A23V 2002/00; A23V 2200/322; A23V 2250/30; A61K 31/35; A61K 35/618; A61K 31/618
See application file for complete search history.

(56) References Cited

U.S. PATENT DOCUMENTS 10,849,934 B2 * 12/2020 Ruan ....................... A23L 33/10

FOREIGN PATENT DOCUMENTS

| CA | 3033547 A1 | 4/2018 |
| CN | 102631371 A | 8/2012 |
| (Continued) |

OTHER PUBLICATIONS

Wheat, Robert W. "Isolation of Uridine Diphosphate-Glycosyl Compounds from the Slug." Science, vol. 132, No. 3436, Nov. 1960, pp. 1310-1311. DOI.org (Crossref), https://doi.org/10.1126/science.132.3436.1310. (Year: 1960).*

(Continued)

*Primary Examiner* — Clinton A Brooks
*Assistant Examiner* — Kyle Nottingham

(57) ABSTRACT

Disclosed is a compound, a preparation method and use thereof. The compound of the application is prepared by extracting and separating from *Limax*, and has significant effects on physiological or psychological dependent detoxification or detoxication. Pharmacological tests have proved that the compound has a significant inhibitory effect on withdrawal jumping symptoms in morphine-dependent animals 1 hour after intragastric administration, and still shows an inhibitory trend after 3 hours. The compound has potential application value in the preparation of medicines, health food, and food for detoxification, detoxication, or similar drug-dependent treatment.

13 Claims, 11 Drawing Sheets

(56) References Cited

FOREIGN PATENT DOCUMENTS

| CN | 103610699 A | 3/2014 |
|---|---|---|
| CN | 107865889 A | 4/2018 |
| CN | 107865890 A | 4/2018 |
| CN | 107868092 A | 4/2018 |
| JP | 2011525550 A | 9/2011 |

OTHER PUBLICATIONS

Liang, Xue, et al. "Limax Extract Ameliorates Cigarette Smoke-Induced Chronic Obstructive Pulmonary Disease in Mice." International Immunopharmacology, vol. 54, Jan. 2018, pp. 210-220. ScienceDirect, https://doi.org/10.1016/j.intimp.2017.11.004. (Year: 2018).*

Shmuel Carmely et al., Neviotine-A, a New Triterpene from the Red Sea Sponge Siphonochalina siphonella, J. Org. Chem., 1985, pp. 784-788, vol. 51, No. 6, American Chemical Society.

International search report of PCT Patent Application No. PCT/CN2019/111538 dated Jan. 8, 2020.

* cited by examiner

Event#: 1 MS(E+)   Ret. Time : 7.417   Scan# : 822

Rank   Score   Formula (M)   Ion   Meas. m/z   Pred. m/z   DBE   Diff (ppm)   Iso Score   Meas. (M)

1   68.94   C36 H58 O10   [M+Na]+   673.3893   673.3922   8.0   -4.31   75.16   650.4001
2   54.58   C43 H54 O5   [M+Na]+   673.3893   673.3863   17.0   4.46   59.75   650.4001
3   12.21   C32 H58 O13   [M+Na]+   673.3893   673.3770   4.0   18.27   68.02   650.4001
4   8.59   C47 H54 O2   [M+Na]+   673.3893   673.4016   21.0   -18.27   47.84   650.4001
5   0.00   C33 H62 O12   [M+Na]+   673.3893   673.4133   3.0   -35.64   72.98   650.4001
6   0.00   C39 H54 O8   [M+Na]+   673.3893   673.3711   13.0   27.03   62.51   650.4001
7   0.00   C40 H58 O7   [M+Na]+   673.3893   673.4075   12.0   -27.03   58.89   650.4001
8   0.00   C28 H58 O16   [M+Na]+   673.3893   673.3617   0.0   40.99   54.82   650.4001
9   0.00   C35 H54 O11   [M+Na]+   673.3893   673.3558   9.0   49.75   53.34   650.4001
10   0.00   C46 H50 O3   [M+Na]+   673.3893   673.3652   22.0   35.79   49.07   650.4001
11   0.00   C44 H58 O4   [M+Na]+   673.3893   673.4227   16.0   -49.60   27.87   650.4001

Rank   Score   Formula (M)   Ion   Meas. m/z   Pred. m/z   DBE   Diff (ppm)   Iso Score   Meas. (M)

1   27.94   C32 H58 O13   [M+K]+   689.3588   689.3509   4.0   11.46   77.39   650.3956
2   25.78   C36 H58 O10   [M+K]+   689.3588   689.3662   8.0   -10.73   67.73   650.3956
3   25.21   C43 H54 O5   [M+K]+   689.3588   689.3603   17.0   -2.18   25.98   650.3956
4   7.83   C39 H54 O8   [M+K]+   689.3588   689.3450   13.0   20.02   58.93   650.3956
5   0.36   C47 H54 O2   [M+K]+   689.3588   689.3755   21.0   -24.23   17.44   650.3956
6   0.00   C35 H54 O11   [M+K]+   689.3588   689.3298   9.0   42.07   67.06   650.3956
7   0.00   C28 H58 O16   [M+K]+   689.3588   689.3356   0.0   33.65   66.93   650.3956
8   0.00   C33 H62 O12   [M+K]+   689.3588   689.3873   3.0   -41.34   54.32   650.3956
9   0.00   C46 H50 O3   [M+K]+   689.3588   689.3392   22.0   28.43   41.54   650.3956
10   0.00   C40 H58 O7   [M+K]+   689.3588   689.3814   12.0   -32.78   25.54   650.3956

COMPOUND, PREPARATION METHOD AND USE THEREOF

CROSS REFERENCE TO RELATED APPLICATION

This application is a continuation-in-part application of PCT application No. PCT/CN2019/111538, filed on Oct. 16, 2019, which claims priority of Chinese patent application No. 201811482596.8 filed on Dec. 5, 2018. The contents of the above-identified applications are all hereby incorporated by reference.

BACKGROUND

Field of the Invention

The present application relates to the field of biomedical chemistry, and specifically, to a compound, a preparation method and use thereof.

Related Arts

Drugs refer to medicines that are used repeatedly and continuously for non-medical purposes and can cause dependence (that is, addiction). There is an increasing number of drug addicts, and their ages are getting younger. Only in China, there are more than 14 million drug addicts, while the number is more than 200 to 400 million in the whole world. Drugs are becoming more and more harmful to the world, and the types of drugs are becoming more and more diverse, from opium and marijuana to heroin, ketamine, methamphetamine, and the like. The proliferation of drugs can directly endanger physical and mental health of people, and brings a huge threat to economic development and social progress.

Detoxication refers to the withdrawal of drug addicts from taking and injecting drugs and the drug addiction. Detoxification treatment for drug addicts may generally include 3 stages: detoxification, rehabilitation, and counseling for re-entering society. Currently, there are 3 commonly used methods for detoxication: natural withdrawal, drug withdrawal, and non-drug withdrawal. The natural withdrawal method is a mandatory detoxication method and lacks humanity. The drug withdrawal method, also known as drug detoxification treatment, refers to a detoxication method by providing and lacks humanity. The drug withdrawal method, also known as drug detoxification treatment, refers to a detoxication method by providing drug addicts with withdrawal drugs to relieve and reduce the withdrawal symptoms in a manner of replacement and decreasing dosage and gradually achieve detoxification, which is the most important detoxication method. Common detoxication drugs may also be classified into 3 categories: opioid chemicals, non-opioid chemicals, and traditional Chinese medicines. However, neither of those detoxication methods can help drug addicts to get rid of drugs physically and psychologically, and they are prone to lapse and relapse. To date, there is no good solutions to this. Therefore, drug detoxication and prohibition have become a worldwide problem. For this reason, people have been trying to find a safe detoxication drug with no dependence.

The traditional Chinese medicines have a long history in detoxication. Compared with the most commonly used replacement treatments such as methadone and naltrexone (both are opioid chemicals), it has the advantages of good compliance, no addiction, definite efficacy on protracted symptoms, and high ethical rate (the proportion of drug addicts who do not relapse after detoxication). Currently, the traditional Chinese medicines used in detoxication are mostly compound preparations evolved on the basis of traditional detoxication recipes. They have many complex effective active ingredients, and their detoxication mechanism cannot be clearly determined. In addition, there are few researches on pharmacology and toxicology, thereby limiting the scientization, standardization, and internationalization of the traditional Chinese medicine compound preparations for detoxication. Therefore, the research on the active ingredients and detoxication mechanism of a single Chinese medicine is beneficial to the use and development of the Chinese medicine detoxication drugs.

*Limax* is a pulmonate mollusk, belonging to the gastropod Gastropoda. Limacidae. Because its body surface is covered with mucus, it is commonly known as "sticky worm, slug, shell less snail, snail, and attached snail". From the perspective of Chinese Medicine, *Limax* is "salty and cold; acting in the lung meridian, the liver meridian, and the large intestine meridian". It has effects of expelling wind for relieving convulsion, and clearing away heat and removing toxic substances. It is mainly used for treating crooked eye and mouth due to apoplexy, tendon and vessel contracture, infantile convulsion, wheeze, pharyngeal swelling, sore throat, carbuncle, subcutaneous nodule, and swelling and pain due to hemorrhoid. The traditional Chinese medicine uses *Limax* to treat disorders such as tumors, asthma, and bronchitis. Existing studies have indicated that *Limax* contains various ingredients such as protein and polysaccharide. Furthermore, the pharmacological studies have found that *Limax* plays a role in anti-tumor, anti-asthma and the like. In recent years, studies on the efficacy of the *Limax* extract have mostly focused on anti-tumor and its effects on respiratory diseases. Among others, the researches on its anti-tumor effects have become a hot spot in domestic and foreign researches. In the researches on the folk prescriptions and secret recipes of Chinese herbal medicine, the inventor found that the *Limax* extract has the efficacy of detoxication treatment, and has been committed to this research. The related active ingredients have been extracted and separated from the *Limax* extract.

SUMMARY

An object of the present application is to provide a compound and a preparation method thereof, which provides a new idea for the research and development of Chinese medicine detoxication products.

The present application uses the following technical solutions:

A compound is provided, which has a structure of:

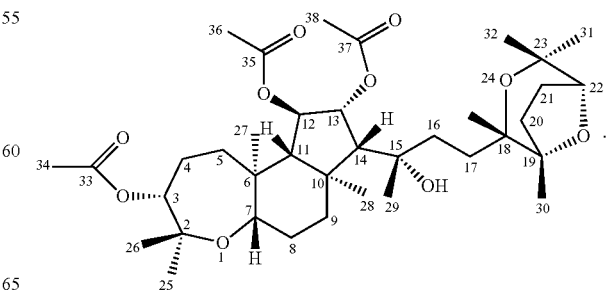

Further, the compound has the chiral C configurations of: C3, R; C6, S; C7, S; C10, S; C11, R; C12, R; C13, R; C14, R; C15, S; C18, S; C19, S; and C22, R.

Further, the compound has a molecular formula: $C_{36}H_{58}O_{10}$; molecular weight: 650; melting point: 228-229° C.; and solubility: white needle-like crystal, insoluble in water, hardly soluble in acid and alkali, easily soluble in ethyl acetate and acetic acid, and soluble in methanol, ethanol, acetone, and chloroform.

Further, the compound is prepared by extracting and separating from *Limax*, wherein the *Limax* comprises one or more of *Vaginulus alte* (Ferussac), *Limax maximus* L., *L. flavus* L., *Agriolimax agrestis* L., and *Phiolomycus bilineatus*.

A method for preparing the compound as described above is provided, including a supercritical $CO_2$ extraction method and a solvent extraction method.

Further, in the method for preparing the compound as described above, the supercritical $CO_2$ extraction method includes the following steps:
R1. sorting *Limax*, removing impurities, and pulverizing, to obtain *Limax* powder;
R2. putting the *Limax* powder into a supercritical $CO_2$ extractor for extraction to obtain an extract:
R3. adding vegetable oil to the extract, heating and mixing evenly, cooling, standing, and filtering to obtain a precipitate, washing the precipitate with a washing solvent, and drying to obtain a dried precipitate; and
R4. adding a crystallization solvent to the dried precipitate, heating to dissolve, cooling, standing to precipitate white needle-like crystals, and filtering to obtain the crystals, recrystallizing, and drying, to obtain the compound.

Furthermore, in the method for preparing the compound as described above, the pulverizing in R1 includes pulverizing into 10-30 meshes.

Furthermore, in the method for preparing the compound as described above, the conditions for the supercritical $CO_2$ extraction in R2 include: pressure: 20-30 kPa, temperature: 60-70° C., flow: 400-500 PV, and extraction time: 3-5 h.

Furthermore, in the method for preparing the compound as described above, the vegetable oil in R3 is tea seed oil, *camellia* seed oil, soybean oil, or olive oil;
the vegetable oil is added in a weight ratio of "extract: vegetable oil=2-6:1-3"
the heating is carried out at a temperature of 60-80° C.;
the time for the standing is 7-10 days; and
the washing includes washing with n-hexane, petroleum ether, or 120#gasoline for 3-5 times, with an amount of 200-500 ml each time.

Furthermore, in the method for preparing the compound as described above, the crystallization solvent in R4 is methanol, acetone, ethyl acetate, or chloroform added at an amount of 3-10 times the weight of the dried precipitate; and the time for the standing is 7-10 days.

Further, in the method for preparing the compound as described above, the solvent extraction method includes the following steps:
S1. sorting *Limax*, removing impurities, and pulverizing, to obtain *Limax* powder;
S2. heating reflux extraction the *Limax* powder with a solvent, filtering, leaving a filtrate and recovering the solvent from the filtrate under reduced pressure until the recovery is complete, to obtain a thick paste;
S3. adding the thick paste to a silica gel chromatography column, eluting with an elution solvent, collecting an eluate, and recovering the elution solvent from the eluate under reduced pressure, to obtain a thick substance; and
S4. adding a dissolution solvent to the thick substance, heating to dissolve completely, cooling, and freezing to precipitate white crystals, filtering, leaving a filtrate, recovering the dissolution solvent from the filtrate under reduced pressure, and re-standing to precipitate white needle-like crystals, filtering, and drying, to obtain the crystals, recrystallizing, and drying, to obtain the compound.

Furthermore, in the method for preparing the compound as described above, the pulverizing in S1 includes pulverizing into 10-30 meshes.

Furthermore, in the method for preparing the compound as described above, the solvent in S2 is one or more of ethanol, methanol, acetone, chloroform, 120#gasoline, n-hexane, petroleum ether, diethyl ether, and ethyl acetate; and the heating reflux extraction includes heating reflux extraction 1-3 times with the solvent, with an amount of 5-15 times the weight of the *Limax* powder each time, for 1-3 h.

Furthermore, in the method for preparing the compound as described above, the adding to the silica gel chromatography column in S3 specifically includes adding silica gel to the thick paste at an amount of 4-6 times the weight of the thick paste, mixing evenly, and adding to the chromatography column pre-filled with silica gel at an amount of 2-4 times the weight of the thick paste; and
the elution solvent is methanol, acetone, or ethyl acetate, and the amount of the elution solvent used is: the volume of the elution solvent: the total weight of the silica gel in the chromatography column=1.5-3:1-2.

Furthermore, in the method for preparing the compound as described above, the dissolution solvent in S4 is methanol or ethanol added in an amount of 4-8 times the volume of the thick substance: the freezing is carried out at a temperature of 2-10° C. for 24 hours; the recovering the solvent from the filtrate under reduced pressure comprises concentrating to 50-60% of the original volume; and the time for the re-standing is 7-10 days.

Furthermore, in the method for preparing the compound as described above, before the eluting with an elution solvent in S3, a step of pre-elution with a pre-elution solvent is performed, wherein the pre-elution solvent is petroleum ether, n-hexane, or 120#gasoline, and the amount of the pre-elution solvent used is: the volume of the pre-elution solvent: the total weight of the silica gel in the chromatography column=–3:0.5-1.5.

Use of the above-mentioned compound in the preparation of medicines, health foods, and food for preventing or treating withdrawal or withdrawal-like symptoms is provided.

Use of the above-mentioned compound in the preparation of medicines, health food, and food for inhibiting withdrawal symptoms in morphine-dependent animals is provided.

The compound of the present application is prepared by separating from the extract of Chinese medicine *Limax* (scientific name: *Agriolima agrestis*) through a simple method, and named 3,12,13-triacetyl limaxol A after identification, with a chemical name of (3R,5aS,7aS,8R,9R,10R,10aR,10bS)-dodecahydro-8-((S)-2-hydroxy-4-((1S,2S,5R)-1,4,4-trimethyl-3,8-dioxa-bicyclo[3.2.1]octan-2-yl)butan-2-yl)-4,4,7a,10b-tetramethyl-1H-indeno[5,4-b]oxepine-3,9,10-triol triacetate. Pharmacological tests have proved that the compound has a significant inhibitory effect on withdrawal jumping symptoms in morphine-dependent animals 1 hour after intragastric administration, and still shows an inhibitory trend after 3 hours, indicating that the compound has significant effects on physiological or psychological dependent detoxification or detoxication, and has potential application value in the preparation of medicines, health food, and food for detoxification, detoxication, or similar drug-dependent treatment.

2: *Limax* crude extract 10 g/kg (1 h);

3: 3,12,13-triacetyl limaxol A 0.5 g/kg (1 h);

4: 3,12,13-triacetyl limaxol A 0.25 g/kg (1 h);

5: 3,12,13-triacetyl limaxol A 0.125 g/kg (1 h); and

6: 3,12,13-triacetyl limaxol A 0.5 g/kg (3 h).

Figure 9A:
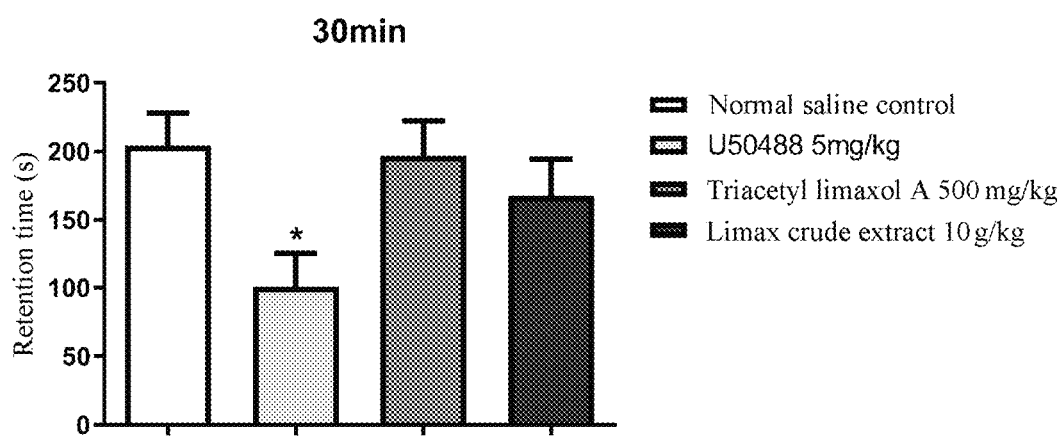

FIG. 9a shows the retention time on the rotarod of the treatment groups 30 minutes after administration in a mouse rotarod model according to Example 11.

Figure 9B:
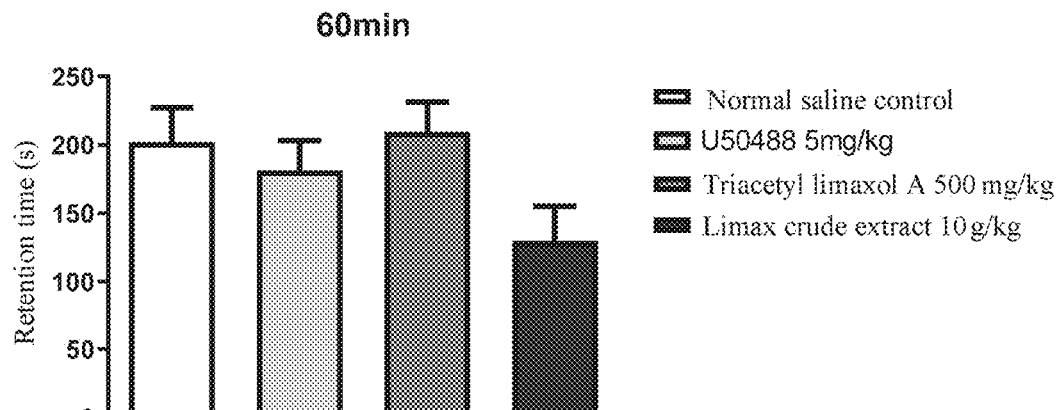

FIG. 9b shows the retention time on the rotarod of the treatment groups 60 minutes after administration in a mouse rotarod model according to Example 11.

Figure 9C:
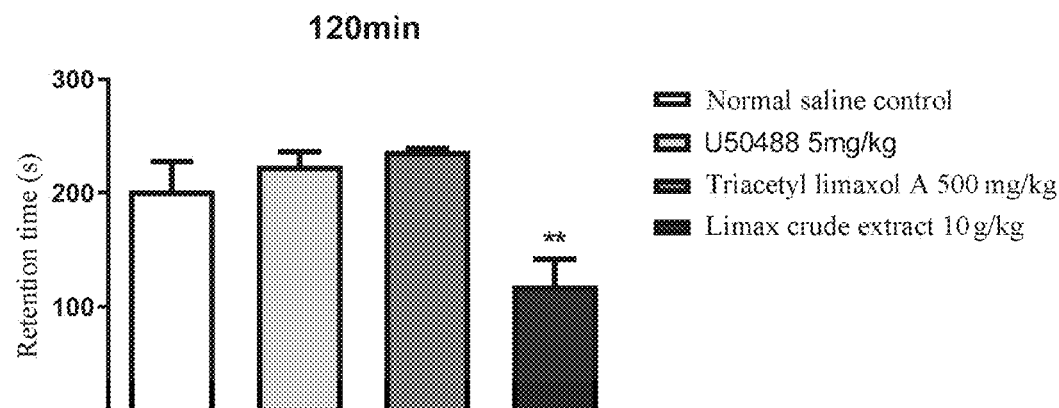

FIG. 9c shows the retention time on the rotarod of the treatment groups 120 minutes after administration in a mouse rotarod model according to Example 11.

Figure 10:
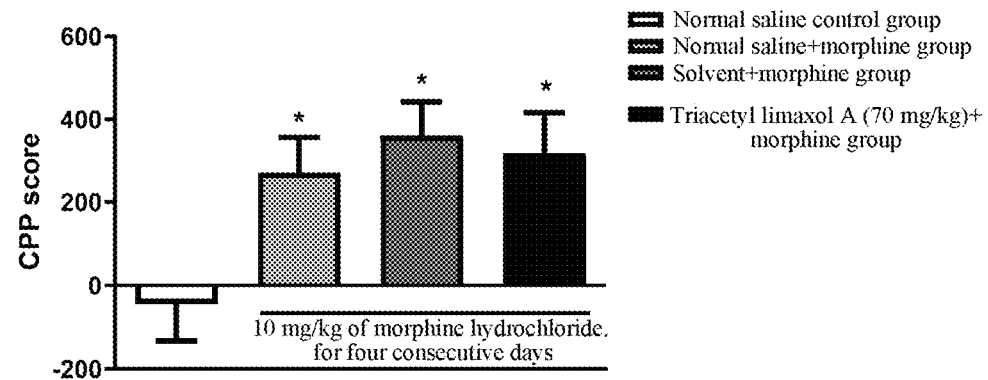

FIG. 10 shows the effect of a single oral administration of triacetyl limaxol A on morphine-induced conditioned place preference behavior in rats according to Example 12.

Figure 11:
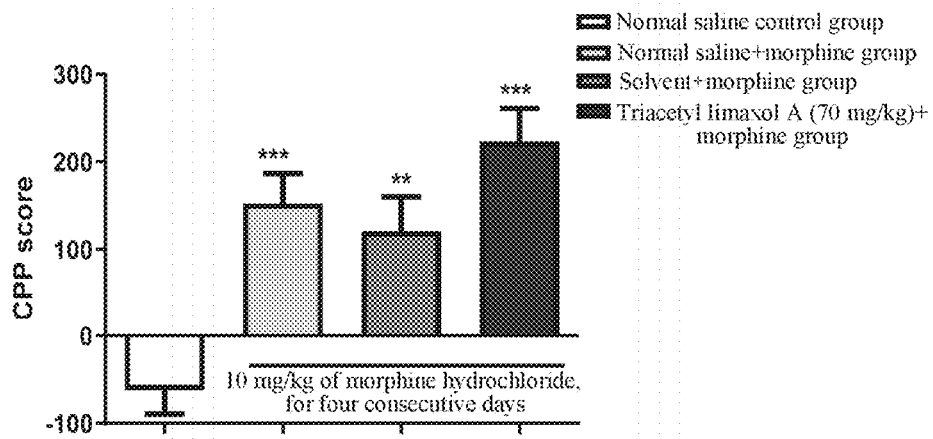

FIG. 11 shows the effect of triacetyl limaxol A on the formation of conditioned place preference induced by morphine in rats according to Example 13.

Figure 12A:
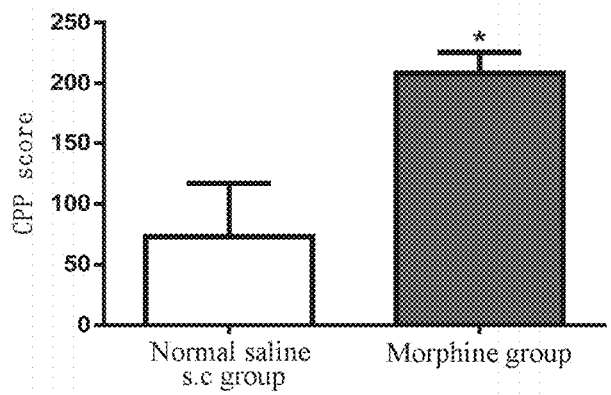

FIG. 12a shows the experimental data of morphine hydrochloride induced conditioned place preference in rats according to Example 14.

Figure 12B:
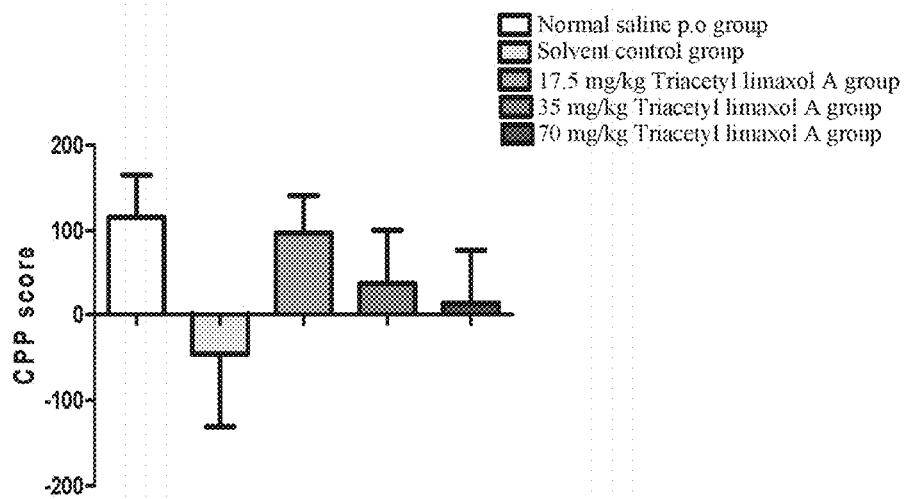

FIG. 12b shows the experimental data of triacetyl limaxol A induced conditioned place preference in rats according to Example 14.

Figure 13:
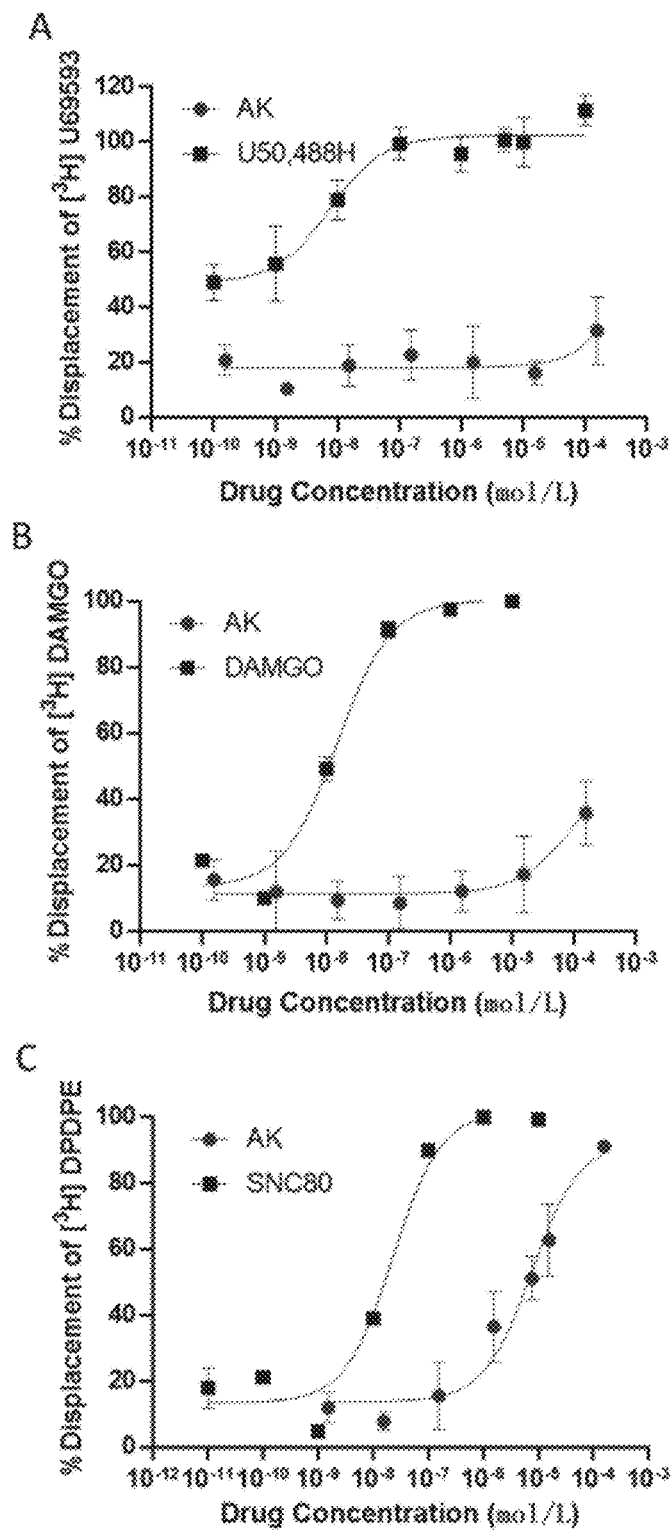

FIG. 13 shows the results of displacement binding assay by the displacement of tritiated U69593, DAMGO and DPDPE with AK and reference ligands at (A) CHO κ, (B) CHO μ and (C) CHO δ cell membranes. Data are means±SEM of n>3 experiments for all cell lines. Reference ligands: U50488, DAMGO and SNC80.

DETAILED DESCRIPTION

I. A Compound

Example 1

The present application provides a compound having a specific structure of:

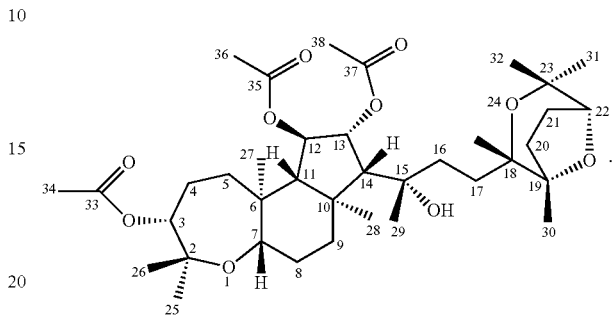

Figure 1:
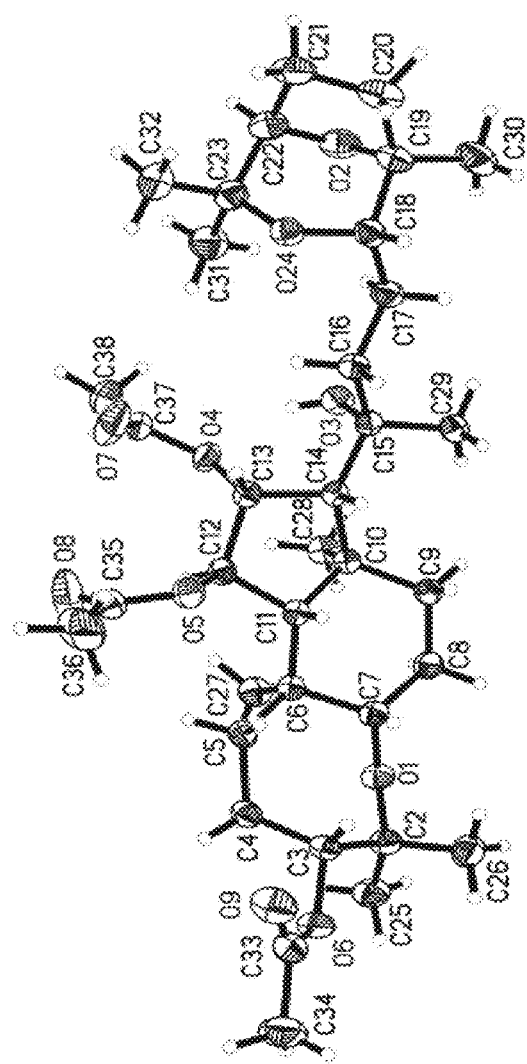
FIG. 1 shows an X-ray crystal structure of the compound according to the present application.
Figure 2:
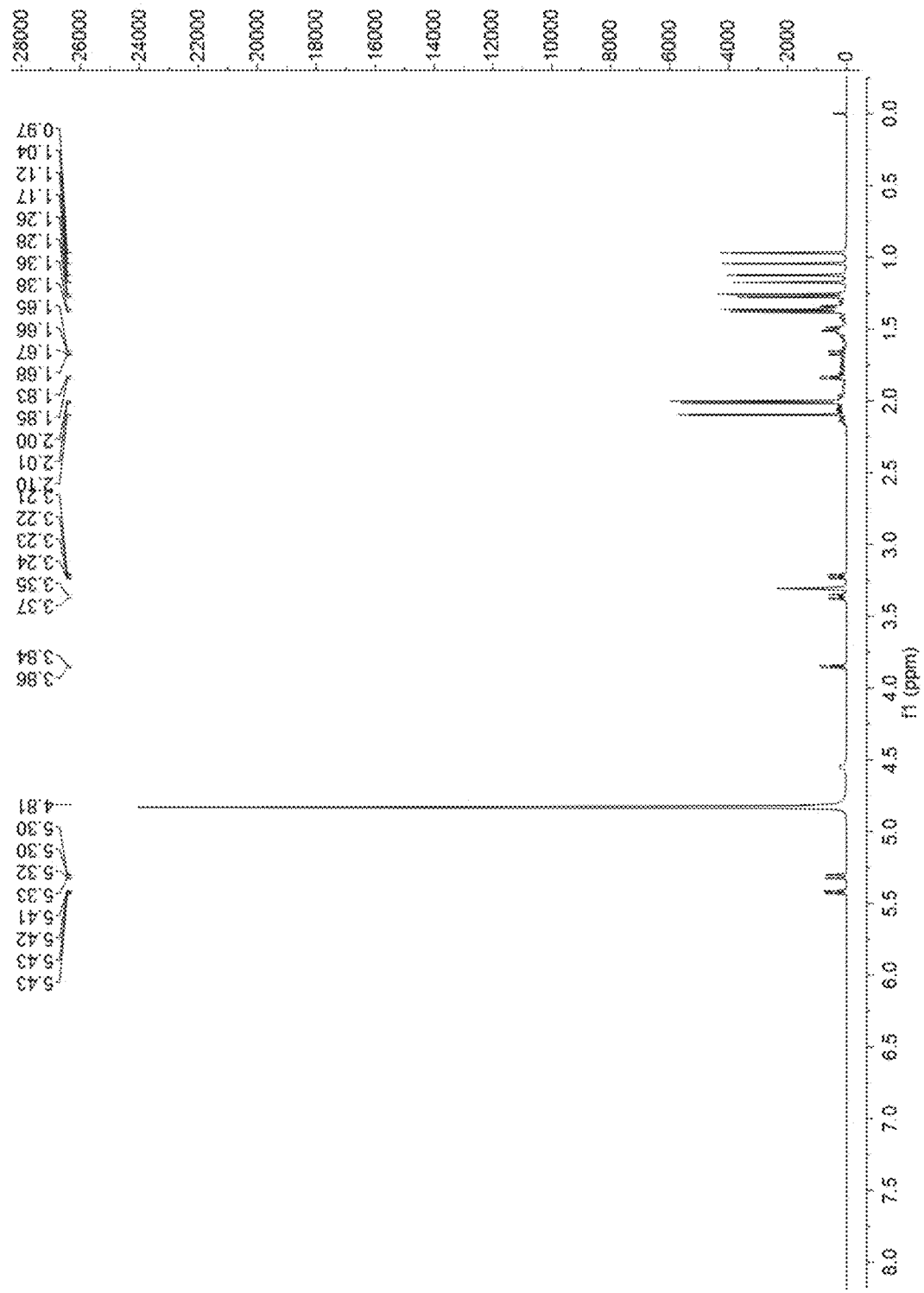
FIG. 2 to FIG. 5 show carbon (C) NMR spectra data and hydrogen (H) NMR spectra data of the compound according to the present application.
Figure 3:
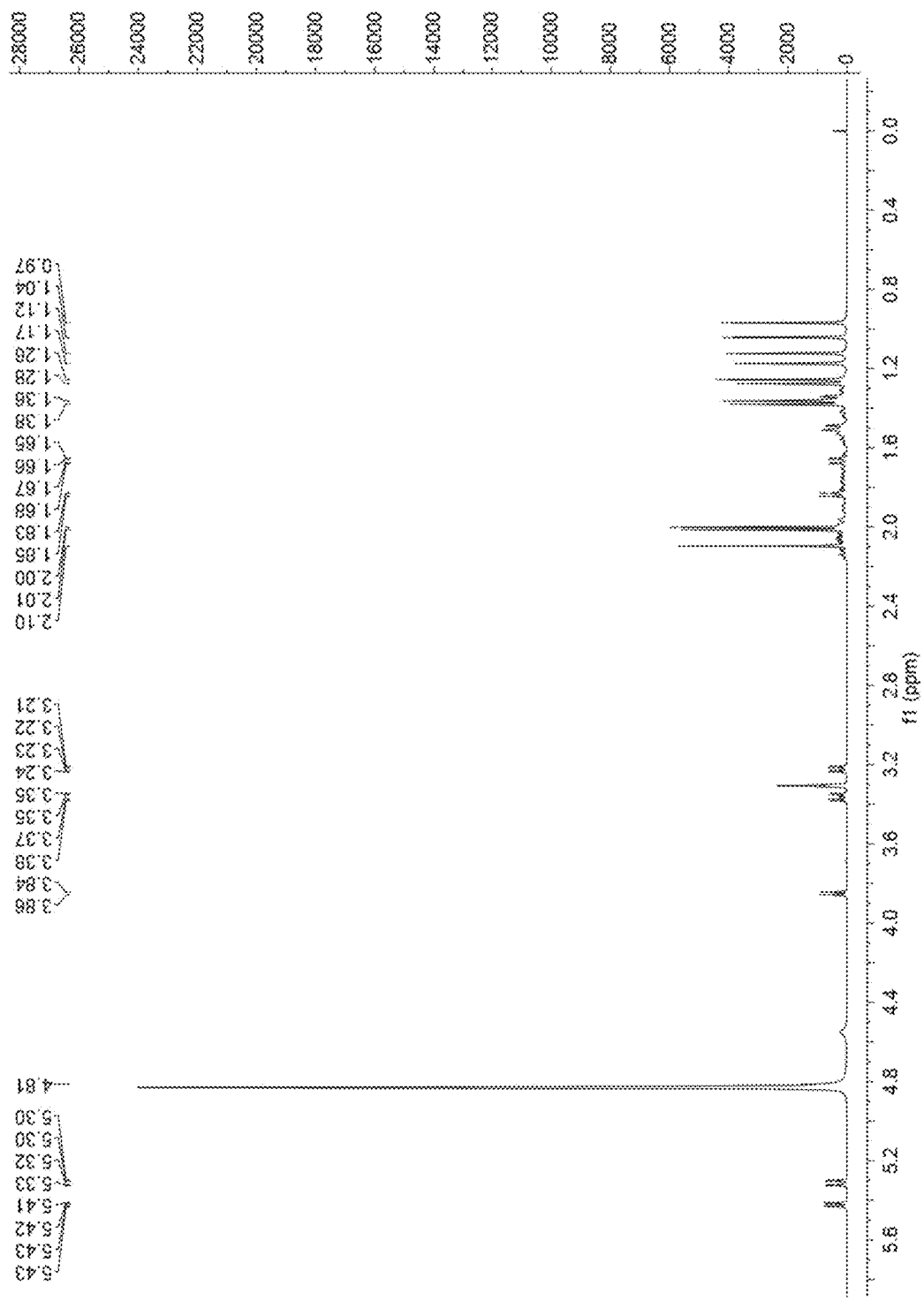
Figure 4:
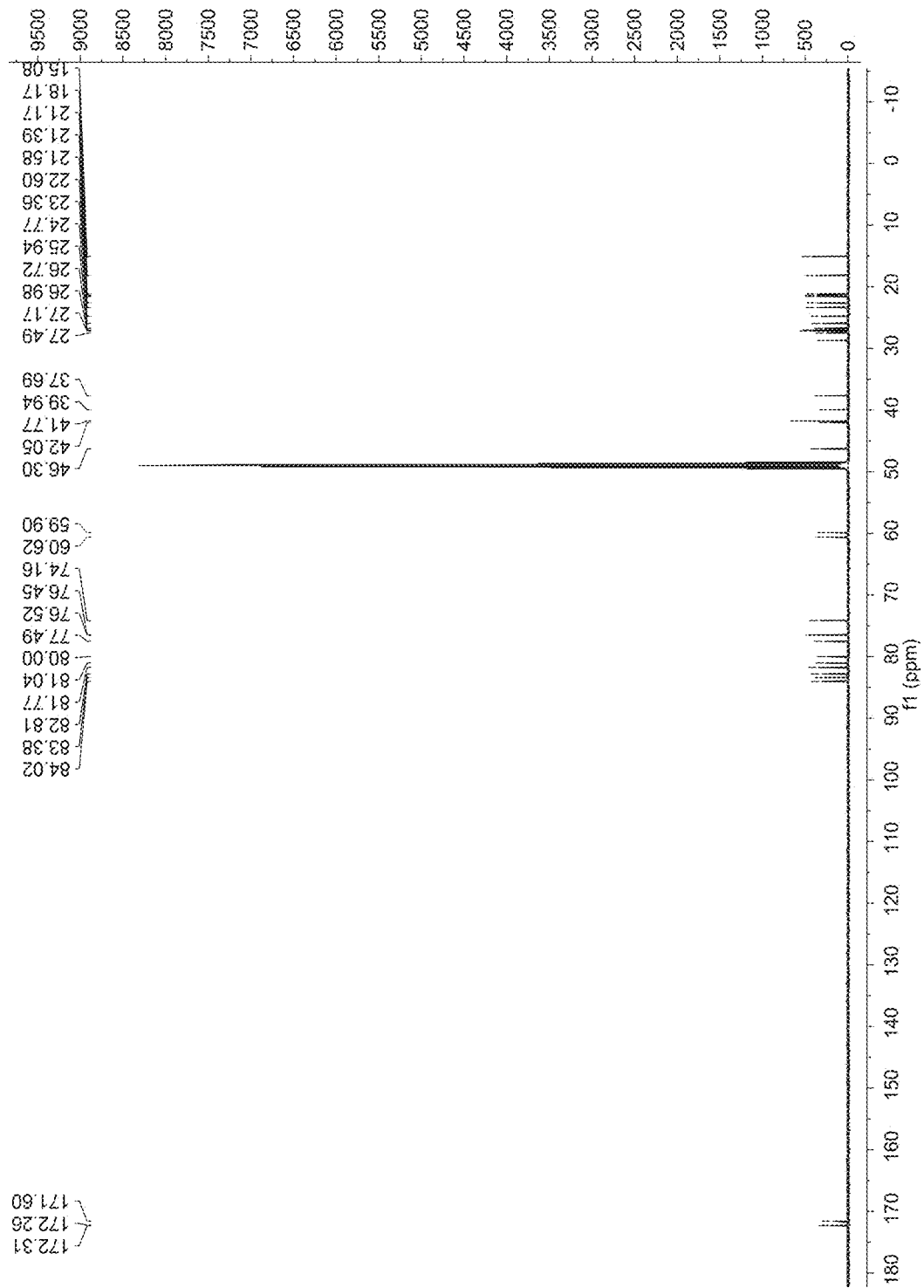
Figure 5:
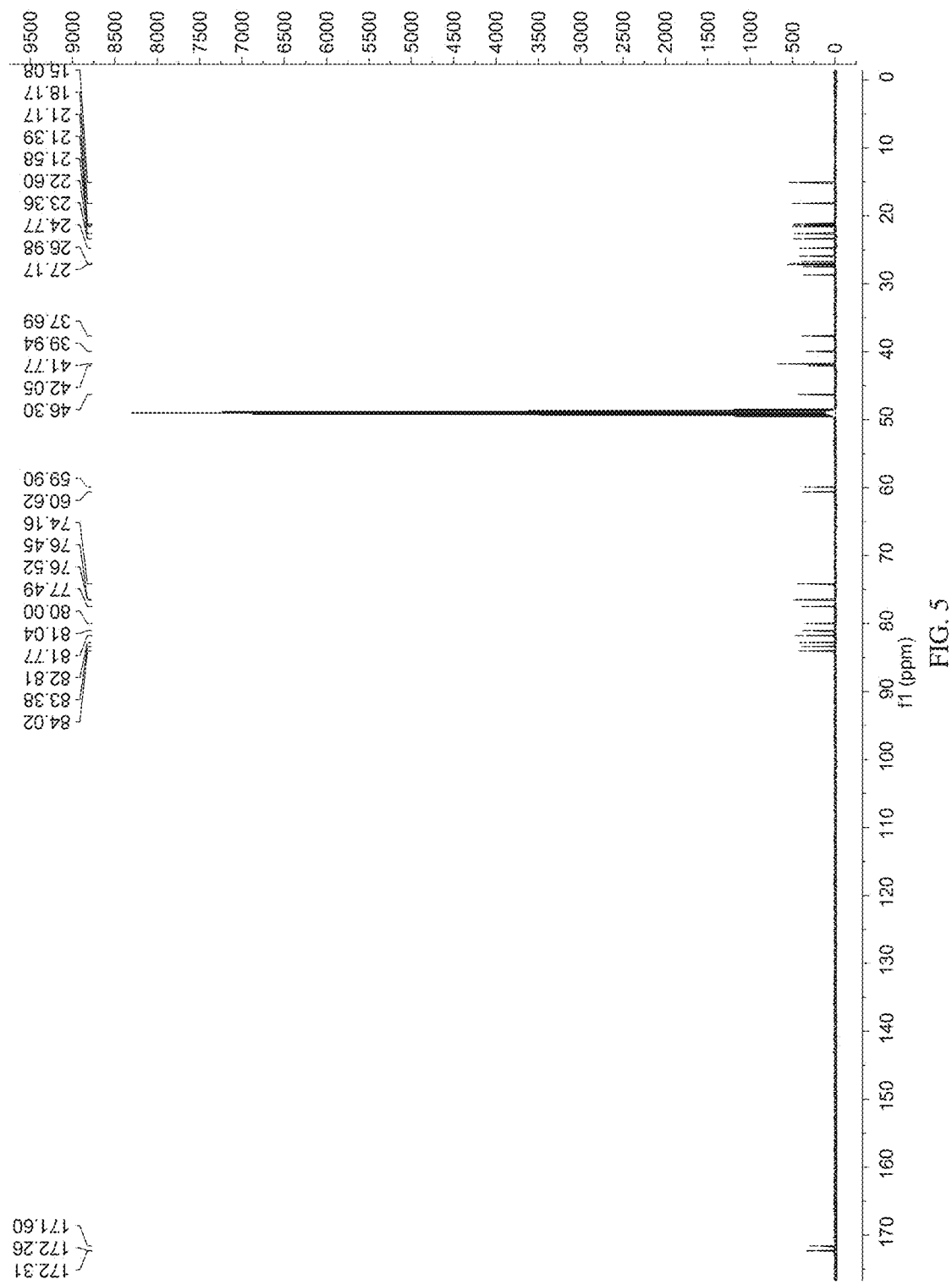

The specific information of the compound is as follows:
(1) The compound is named "3,12,13-triacetyl limaxol A";
(2) Chiral C configurations of the compound include: C3, R; C6, S; C7, S; C10, S; C11, R; C12, R; C13, R; C14, R; C15, S; C18, S; C19, S; and C22, R with the crystal structure shown in FIG. 1;
(3) Physical and chemical properties and spectra data include:
① molecular formula: $C_{36}H_{58}O_{10}$; molecular weight 650;
② state: white needle-like crystals;
③ melting point: 228-229° C.;
④ solubility: insoluble in water, hardly soluble in acid and alkali, easily soluble in ethyl acetate and acetic acid, and soluble in methanol, ethanol, acetone, and chloroform;
⑤ carbon (C) and hydrogen (H) NMR spectra data, as shown in Table 1 and FIG. 2 to FIG. 5;

TABLE 1

NMR data
MR2
$^{13}C$ and $^1H$-NMR data (500 MHz, in $CD_3OD$)

| NO | $\delta_C$ | $\delta_H$ (J in Hz) |
|---|---|---|
| 1 | | |
| 2 | 76.5 | |
| 3 | 81.0 | 4.82 (d, J = 9.8 Hz, 1H) |
| 4 | 27.5 | 2.01, 2.05 (m, 2H) |
| 5 | 42.1 | 1.36 (m, 2H) |
| 6 | 41.8 | |
| 7 | 77.5 | 3.37 (dd, J = 11.6, 4.5 Hz, 1H) |
| 8 | 28.7 | 1.51, 1.72 (m, 2H) |
| 9 | 39.9 | 1.51, 1.98 (m, 2H) |
| 10 | 46.3 | |
| 11 | 60.6 | 1.50 (d, J = 11.5 Hz, 1H) |
| 12 | 80.0 | 5.31 (dd, J = 11.5, 2.5 Hz, 1H) |
| 13 | 83.4 | 5.42 (dd, J = 7.6, 2.5 Hz, 1H) |
| 14 | 59.9 | 1.84 (d, J = 7.6 Hz, 1H) |
| 15 | 76.5 | |
| 16 | 41.8 | 1.76-1.79 (m, 2H) |
| 17 | 27.2 | 1.57, 1.91 (m, 2H) |
| 18 | 82.8 | 3.22 (dd, J = 10.8, 4.0 Hz, 1H) |
| 19 | 81.8 | |
| 20 | 37.7 | 1.66, 2.06 (m, 2H) |
| 21 | 25.9 | 1.83, 2.14 (m, 2H) |

TABLE 1-continued

NMR data
MR2
$^{13}$C and $^1$H-NMR data (500 MHz, in CD$_3$OD)

| NO | $\delta_C$ | $\delta_H$ (J in Hz) |
|---|---|---|
| 22 | 84.0 | 3.85 (d, J = 7.0 Hz, 1H) |
| 23 | 74.2 | |
| 24 | | |
| 25 | 23.4 | 1.12 (s, 3H) |
| 26 | 24.8 | 1.17 (s, 3H) |
| 27 | 15.1 | 0.97 (s, 3H) |
| 28 | 18.2 | 1.36 (s, 3H) |
| 29 | 26.7 | 1.28 (s, 3H) |
| 30 | 22.6 | 1.26 (s, 3H) |
| 31 | 27.0 | 1.04 (s, 3H) |
| 32 | 27.2 | 1.38 (s, 3H) |
| 33 | 171.6 | |
| 34 | 21.6 | 2.10 (s, 3H) |
| 35 | 172.3 | |
| 36 | 21.4 | 2.02 (s, 3H) |
| 37 | 172.3 | |
| 38 | 21.2 | 2.00 (s, 3H) |

Figure 6:
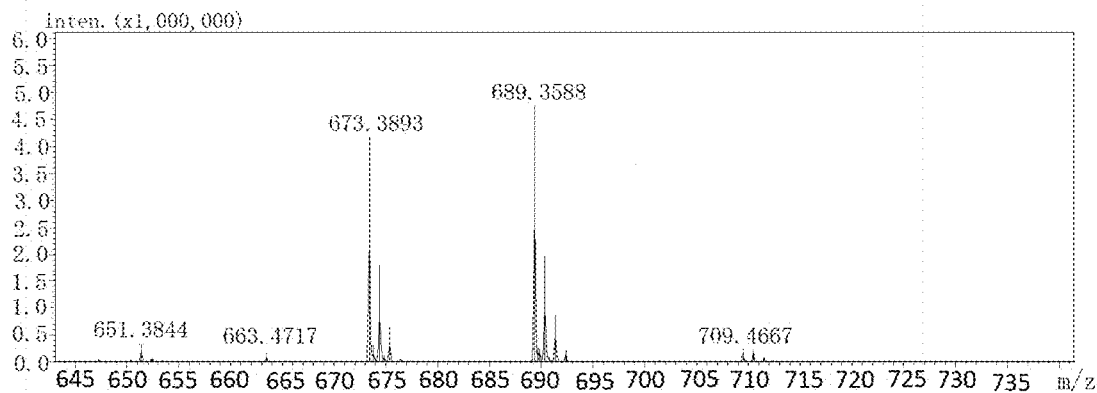
FIG. 6 shows mass spectrometry (MS) data of the compound according to the present application.
Figure 7:
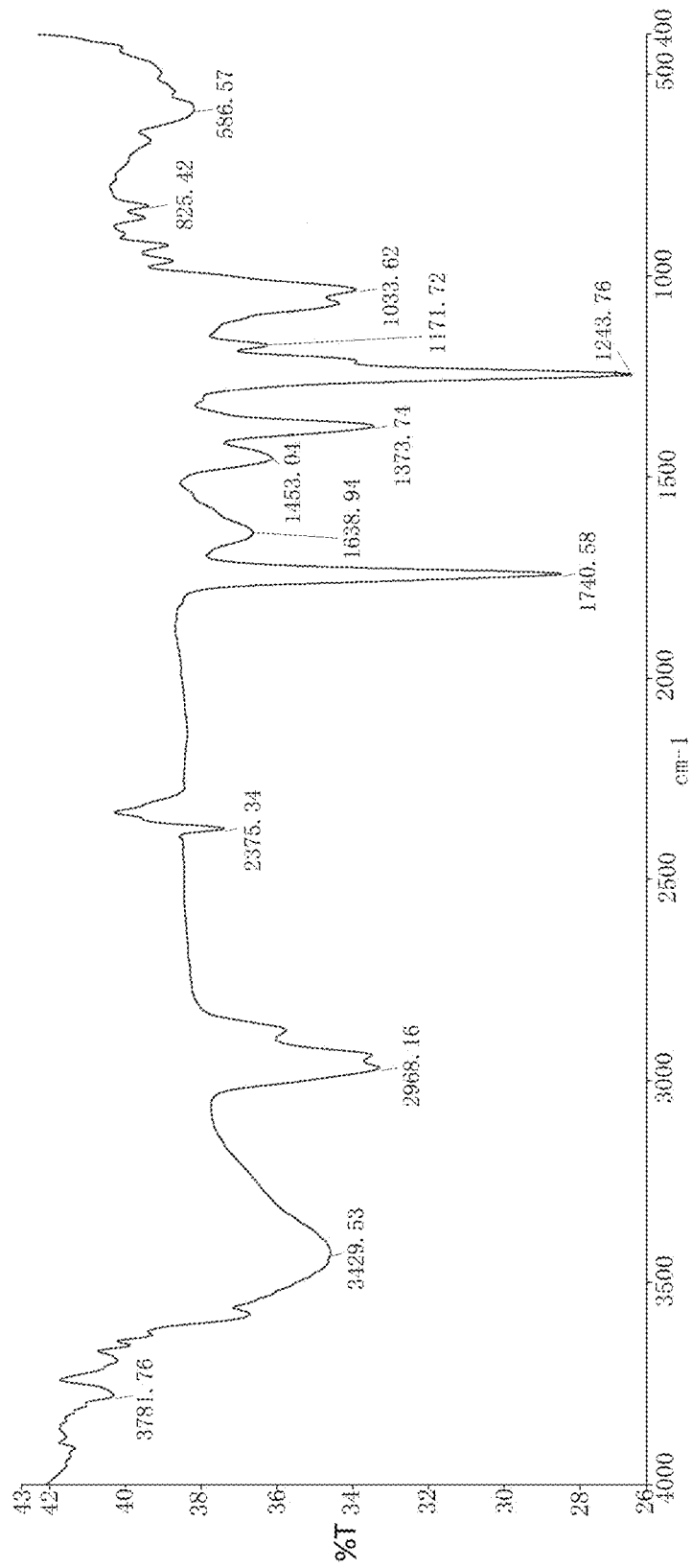
FIG. 7 shows infrared (IR) spectroscopy data of the compound according to the present application.

⑥ mass spectrometry (MS) data, as shown in FIG. 6 and
⑦ infrared (IR) spectroscopy data, as shown in FIG. 7.

II. A Method for Preparing a Compound

Example 2

A method for preparing a compound (a supercritical CO$_2$ extraction method) includes the following steps:
R1. *Limax*, after sorting and removing impurities, was pulverized into 30 mesh powder for later use;
R2. 50 kg of *Limax* powder was put into a supercritical CO$_2$ extractor for extraction under the extraction conditions: pressure 20 kPa, temperature 60° C., flow 400-500 PV, and extraction time 3 h, obtaining 2.9 kg of ointment-like extract for later use;
R3. tea seed oil was added to the extract in a weight ratio of "extract: tea seed oil=2:1", that is, 2.9 kg of the extract and 1.45 kg of tea seed oil were put into a mixing tank; the mixture was heated at 60° C., mixed evenly, cooled and stood for 7 days to precipitate, and then filtered to obtain 198 g of precipitate; the precipitate was washed with petroleum ether (200 ml×3) under heating, and then dried, to obtain 123 g of precipitate; and
R4. the precipitate was added to 800 ml of methanol, and dissolved by heating, cooled, and stood for 7 days to precipitate white needle-like crystals, filtered to obtain the crystals; an appropriate amount of ethyl acetate was added to dissolve the crystals, filtered, and the filtrate was stood for 7 days to precipitate white needle-like crystals, filtered and dried to obtain 95.4 g of the compound, 3,12,13-triacetyl limaxol A.

Example 3

A method for preparing a compound (a supercritical CO$_2$ extraction method) includes the following steps:
R1. *Limax*, after sorting and removing impurities, was pulverized into 20 mesh powder for later use;
R2. 60 kg of *Limax* powder was put into a supercritical CO$_2$ extractor for extraction under the extraction conditions: pressure 25 kPa, temperature 65° C., flow 400-500 PV, and extraction time 4 h, obtaining 3.5 kg of ointment-like extract for later use;
R3. soybean oil was added to the extract in a weight ratio of "extract: soybean oil=4:2", that is, 3.5 kg of the extract and 1.75 kg of soybean oil were put into a mixing tank; the mixture was heated at 65° C., mixed evenly, cooled and stood for 8 days, and then filtered to obtain 235 g of precipitate; the precipitate was washed with n-hexane (300 ml×3), and then dried, to obtain 151 g of precipitate; and
R4. the precipitate was added to 500 ml of ethyl acetate, and heated to dissolve, cooled, and stood for 8 days to precipitate white needle-like crystals, and filtered to obtain the crystals; an appropriate amount of ethyl acetate was added to dissolve the crystals, filtered, and the filtrate was stood for 8 days to precipitate white needle-like crystals, filtered and dried to obtain 116.0 g of the compound, 3,12,13-triacetyl limaxol A.

Example 4

A method for preparing a compound (a supercritical CO$_2$ extraction method) includes the following steps:
R1. *Limax*, after sorting and removing impurities, was pulverized into 20 mesh powder for later use;
R2. 100 kg of *Limax* powder was put into a supercritical CO$_2$ extractor for extraction under the extraction conditions: pressure 28 kPa, temperature 68° C., flow 400-500 PV, and extraction time 4.5 h, obtaining 5.9 kg of ointment-like extract for later use;
R3. olive oil was added to the extract in a weight ratio of "extract: olive oil=5:2.5", that is, 5.9 kg of the extract and 2.95 kg of olive oil were put into a mixing tank; the mixture was heated at 70° C., mixed evenly, cooled and stood for 9 days, and then filtered to obtain 393 g of precipitate; the precipitate was washed with 120$^\#$gasoline (400 ml×4), and then dried, to obtain 255 g of precipitate; and
R4. the precipitate was added to 2200 ml of acetone, and heated to dissolve, cooled, and stood for 9 days to precipitate white needle-like crystals, and filtered to obtain the crystals; an appropriate amount of ethyl acetate was added to dissolve the crystals, filtered, and the filtrate was stood for 9 days to precipitate white needle-like crystals, filtered and dried to obtain 196.1 g of the compound, 3,12,13-triacetyl limaxol A.

Example 5

A method for preparing a compound (a supercritical CO$_2$ extraction method) includes the following steps:
R1. *Limax*, after sorting and removing impurities, was pulverized into 10 mesh powder for later use;
R2. 150 kg of *Limax* powder was put into a supercritical CO$_2$ extractor for extraction under the extraction conditions: pressure 30 kPa, temperature 70° C., flow 400-500 PV, and extraction time 5 h, obtaining 8.7 kg of ointment-like extract for later use;
R3. *camellia* seed oil was added to the extract in a weight ratio of "extract: *camellia* seed oil=6:3", that is, 8.7 kg of the extract and 4.36 kg of *camellia* seed oil were put into a mixing tank; the mixture was heated at 80° C., mixed evenly, cooled and stood for 10 days, and then filtered to obtain 581 g of precipitate; the precipitate was washed with n-hexane (500 ml×5), and then dried, to obtain 372 g of precipitate; and
R4. the precipitate was added to 5000 ml of chloroform, and heated to dissolve, cooled, and stood for 10 days to precipitate white needle-like crystals, and filtered to obtain the crystals; an appropriate amount of ethyl acetate was added to dissolve the crystals, filtered, and the filtrate was stood for 10 days to precipitate white needle-like crystals, filtered and dried to obtain 287.3 g of the compound, 3,12,13-triacetyl limaxol A.

Example 6

A method for preparing a compound (a solvent extraction method) includes the following steps:
S1. *Limax*, after sorting and removing impurities, was pulverized into 20 mesh powder for later use;
S2. 100 kg of *Limax* powder was put into a multi-functional extraction tank, and extracted at reflux with n-hexane for 2 times, firstly with an amount of 10 times the weight of the *Limax* powder for 1.5 h, and then with an amount of 8 times the weight of the *Limax* powder for 1.0 h; each of the extracts was filtered, and the filtrates were combined, and the n-hexane was recovered under reduced pressure until the recovery was complete, to obtain 8.10 kg of an oily thick paste;
S3. 40.5 kg of silica gel was added to the thick paste and mixed evenly; the mixture was added to a chromatography column pre-filled with 24.3 kg of silica gel, and pre-eluted with petroleum ether in the ratio of "the volume of petroleum ether: the total weight of the silica gel in the chromatography column=2:1" (that is, 129.6 L of petroleum ether), and then eluted with ethyl acetate in the ratio of "the volume of ethyl acetate: the total weight of the silica gel in the chromatography column=2.25:1.5" (that is, 97.2 L of ethyl acetate), the ethyl acetate eluate was collected, and concentrated under reduced pressure to recover ethyl acetate, thereby obtaining 4.3 kg of a thick substance; and
S4. 27.0 L of methanol was added to the thick substance, heated to dissolve completely, and frozen at 6° C. for 24 hours, to precipitate white crystals, filtered, and the filtrate was concentrated under reduced pressure to recover about 14.9 L of methanol, and then stood for 9 days to precipitate white needle-like crystals, filtered and dried to obtain 359 g of crystals, 1.0 L of ethyl acetate was added to the crystals, heated to dissolve, cooled, and stood for 9 days, to precipitate white needle-like crystals, filtered and dried to obtain 210.4 g of the compound, 3,12,13-triacetyl limaxol A.

Example 7

A method for preparing a compound (a solvent extraction method) includes the following steps:
S1. *Limax*, after sorting and removing impurities, was pulverized into 30 mesh powder for later use;
S2. 50 kg of *Limax* powder was put into a multi-functional extraction tank, and extracted at reflux with a mixed solvent (methanol:diethyl ether:ethyl acetate=1:1:1) at an amount of 15 times the weight of the *Limax* powder for 3 h, filtered, and the mixed solvent was recovered from the filtrate under reduced pressure until the recovery was complete, to obtain 3.98 kg of an oily thick paste;
S3. 23.8 kg of silica gel was added to the thick paste and mixed evenly: the mixture was added to a chromatography column pre-filled with 15.9 kg of silica gel, and pre-eluted with 120$^\#$gasoline in the ratio of "the volume of 120$^\#$gasoline: the total weight of the silica gel in the chromatography column=1:0.5" (that is, 79.4 L of 120$^\#$gasoline), and then eluted with methanol in the ratio of "the volume of methanol: the total weight of the silica gel in the chromatography column=1.5:1" (that is, 59.5 L of methanol), the methanol eluate was collected, and concentrated under reduced pressure to recover methanol, thereby obtaining 2.07 kg of a thick substance; and
S4. 13.0 L of ethanol was added to the thick substance, heated to dissolve completely, and frozen at 10° C. for 24 hours, to precipitate white crystals, filtered, and the filtrate was concentrated under reduced pressure to recover about 6.5 L of ethanol, and then stood for 7 days to precipitate white needle-like crystals, filtered and dried to obtain 178.1 g of crystals, 500 ml of ethyl acetate was added to the crystals, heated to dissolve, cooled, and stood for 7 days, to precipitate white needle-like crystals, filtered and dried to obtain 103.8 g of the compound, 3,12,13-triacetyl limaxol A.

Example 8

A method for preparing a compound (a solvent extraction method) includes the following steps:
S1. *Limax*, after sorting and removing impurities, was pulverized into 10 mesh powder for later use;
S2. 150 kg of *Limax* powder was put into a multi-functional extraction tank, and extracted at reflux with a mixed solvent (ethanol:acetone=1:1) for 3 times, firstly with an amount of 12 times the weight of the *Limax* powder for 2.5 h, secondly with an amount of 8 times the weight of the *Limax* powder for 1.5 h, thirdly with an amount of 5 times the weight of the *Limax* powder for 1 h; each of the extracts was filtered, and the filtrates were combined, and the mixed solvent was recovered under reduced pressure until the recovery was complete, to obtain 11.98 kg of an oily thick paste;
S3. 48.4 kg of silica gel was added to the thick paste and mixed evenly; the mixture was added to a chromatography column pre-filled with 24.3 kg of silica gel, and pre-eluted with n-hexane in the ratio of "the volume of n-hexane: the total weight of the silica gel in the chromatography column=3:1.5" (that is, 146.3 L of n-hexane), and then eluted with acetone in the ratio of "the volume of acetone: the total weight of the silica gel in the chromatography column=3:2" (that is, 110.8 L of acetone), the acetone eluate was collected, and concentrated under reduced pressure to recover acetone, thereby obtaining 6.3 kg of a thick substance; and
S4. 40.0 L of methanol was added to the thick substance, heated to dissolve completely, and frozen at 2° C. for 24 hours, to precipitate white crystals, filtered, and the filtrate was concentrated under reduced pressure to recover about 24 L methanol, and then stood for 10 days to precipitate white needle-like crystals, filtered and dried to obtain 534 g of crystals, 1.5 L of ethyl acetate was added to the crystals, heated to dissolve, cooled, and stood for 10 days, to precipitate white needle-like crystals, filtered and dried to obtain 311.2 g of the compound, 3,12,13-triacetyl limaxol A.

Example 9

A method for preparing a compound (a solvent extraction method) includes the following steps:
S1. *Limax*, after sorting and removing impurities, was pulverized into 20 mesh powder for later use;
S2. 70 kg of *Limax* powder was put into a multi-functional extraction tank, and extracted at reflux with a mixed solvent (chloroform: petroleum ether: 120#gasoline: n-hexane=1:2:1:6) for 2 times, firstly with an amount of 13 times the weight of the *Limax* powder for 2 h, and then with an amount of 6 times the weight of the *Limax* powder for 1.0 h: each of the extracts was filtered, and the filtrates were combined, and the mixed solvent was recovered under reduced pressure until the recovery was complete, to obtain 5.52 kg of an oily thick paste;

S3. 24.8 kg of silica gel was added to the thick paste and mixed evenly: the mixture was added to a chromatography column pre-filled with 13.8 kg of silica gel, and pre-eluted with petroleum ether in the ratio of "the volume of petroleum ether: the total weight of the silica gel in the chromatography column=2.4:1.2" (that is, 77.2 L of petroleum ether), and then eluted with ethyl acetate in the ratio of "the volume of ethyl acetate: the total weight of the silica gel in the chromatography column=1.8:1.2" (that is, 57.9 L of ethyl acetate), the ethyl acetate eluate was collected, and concentrated under reduced pressure to recover ethyl acetate, to obtain 2.90 kg of a thick substance; and S4. 18.3 L of ethanol was added to the thick substance, heated to dissolve completely, and frozen at 8° C. for 24 hours, to precipitate white crystals, filtered, and the filtrate was concentrated under reduced pressure to recover about 9.6 L of ethanol, and then stood for 8 days to precipitate white needle-like crystals, filtered and dried to obtain 252.0 g of crystals, 0.7 L of ethyl acetate was added to the crystals, heated to dissolve, cooled, and stood for 8 days, to precipitate white needle-like crystals, filtered and dried to obtain 148.2 g of the compound, 3,12,13-triacetyl limaxol A.

III. Pharmacological Tests

Example 10

Experiment on the effect of the *Limax* extract on morphine-induced physical dependence 1. Object of Experiment This experiment aims to study the effect of the *Limax* extract on morphine-induced physical dependence symptoms.

2. Materials and Method 2.1 Materials 2.1.1 Test samples

The *Limax* extract was provided by Guangxi Jiufu Biotechnology Co., Ltd., the *Limax* crude extract was an ointment-like extract obtained by the supercritical $CO_2$ extraction in R2 in Example 3 of the present application, and the 3,12,13-triacetyl limaxol A was a sample prepared in Example 3 of the present application; the morphine hydrochloride injection was commercially available from Shenyang No. 1 Pharmaceutical Factory of NORTHEAST PHARM; and the methadone was commercially available from Tianjin Central Pharmaceutical Industry Co., Ltd.

2.1.2 Experiment Animals

Kunming mice, males, weighing 18-22 g, were commercially available from Shanghai SiJie Laboratory Animal Co., Ltd.

2.2 Method 2.2.1 Effect on Morphine-Induced Physical Symptoms

The animals were randomized into a normal saline group, a model group, a positive control group (methadone), and test medicine groups at different doses. Each group has at least 8 mice. The normal saline group was given normal saline every day. The animals in the morphine model group, the positive control group, and the test medicine groups were given morphine at increasing doses of 10, 20, 40, 80, 100 mg/kg by subcutaneous administration twice a day, with a 6-hour interval between each administration. From day 3, 100 mg/kg of morphine was administrated for 7 consecutive days. On day 8, 4 mg/kg of naloxone was administered intraperitoneally 4 hours after the administration of morphine, and the number of jumpings within 30 minutes was recorded. At different time points (1 hour or 3 hours) before naloxone administration, the vehicle control, the positive control, and the test medicine were dosed intragastrically.

2.2.2 Statistical Analysis

The experiment results were represented by Mean±SEM, and differences between groups are tested by t-test. $P<0.05$ showed a significant difference.

3. Results

Effect of the *Limax* Extract on Morphine-Induced Physical Dependence Symptoms

Figure 8:
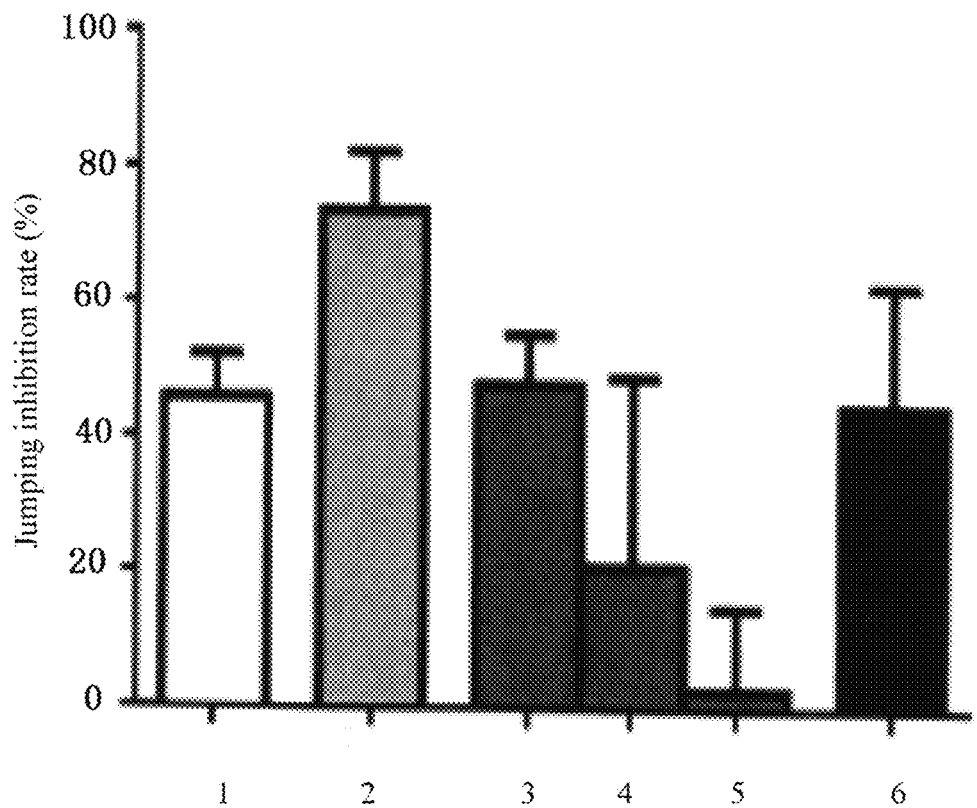
FIG. 8 shows inhibition rates of methadone, *Limax* extract, and different doses of 3,12,13-triacetyl limaxol A on morphine-withdrawal jumping symptoms, where: 1: methadone 20 mg/kg (1 h)

The experiment results were shown in Table 2 to Table 4. After chronic morphine treatment, naloxone was administrated to induce withdrawal responses, and the animals showed significant withdrawal jumping symptoms. The withdrawal jumping symptoms of the animals were significantly reduced 1 hour after the methadone (20 mg/kg) administration, 3 hours after the *Limax* crude extract (10 g/kg) administration, and 1 hour after the 3,12,13-triacetyl limaxol A (0.5 g/kg) administration. Table 5 showed that the withdrawal jumping symptoms of the animals tended to be reduced 3 hours after the 3,12,13-triacetyl limaxol A (0.5 g/kg) administration, but there was no significant difference from the model group. FIG. 8 showed inhibition rates of three drugs on morphine-withdrawal jumping symptoms, in an order of *Limax* crude extract (10 g/kg, −3 h)>3,12,13-triacetyl limaxol A (0.5 g/kg, −1 h)≈methadone (20 mg/kg, −1 h).

TABLE 2

Effect of methadone on morphine-withdrawal jumping symptoms

| Group | Jumping times (Mean ± SEM) | % Inhibition of morphine-withdrawal jumping |
|---|---|---|
| Normal saline | 0.3 ± 0.3 | — |
| Morphine | 62.4 ± 12.7*** | — |
| Morphine + methadone 20 mg/kg | 33.8 ± 3.3* | 46.1 ± 5.2 |

The results in Table 2 showed that there was a significant difference between the morphine group and the control group (**$P<0.001$), indicating that naloxone administration after chronic morphine treatment can induce significant withdrawal jumping symptoms. There was a significant difference between the morphine+methadone group and the morphine group (*$P<0.05$), indicating that the withdrawal jumping symptoms induced by naloxone administration can be significantly reduced 1 hour after the methadone (20 mg/kg) administration.

TABLE 3

Effect of the Limax crude extract on morphine-withdrawal jumping symptoms

| Group | Jumping times (Mean ± SEM) | % Inhibition of morphine-withdrawal jumping |
|---|---|---|
| Normal saline | 0.0 ± 0.0 | — |
| Morphine | 54.8 ± 14.1** | — |
| Morphine + Limax crude extract 10 g/kg | 14.3 ± 4.7* | 73.9 ± 8.6 |

The results in Table 3 showed that there was a significant difference between the morphine group and the control group (**P<0.01), indicating that naloxone administration after chronic morphine treatment can induce significant withdrawal jumping symptoms. There was a significant difference between the morphine+*Limax* crude extract group and the morphine group (*P<0.05), indicating that the withdrawal jumping symptoms induced by naloxone administration can be significantly reduced 3 hours after the *Limax* crude extract (10 g/kg) administration.

TABLE 4

Effect of 3,12,13-triacetyl limaxol A on morphine-withdrawal jumping symptoms 1 hour after administration

| Group | Jumping times (Mean ± SEM) | % Inhibition of morphine-withdrawal jumping |
|---|---|---|
| Normal saline | 1.3 ± 0.8 | — |
| Morphine | 34.5 ± 5.2*** | — |
| Morphine ++ 3,12,13-triacetyl limaxol A 0.5 g/kg | 18.5 ± 2.4 | 48.2 ± 7.5 |
| Morphine + 3,12,13-triacetyl limaxol A 0.25 g/kg | 27.5 ± 9.4 | 21.1 ± 28.2 |
| Morphine + 3,12,13-triacetyl limaxol A 0.125 g/kg | 33.5 ± 4.1 | 3.0 ± 12.2 |

The results in Table 4 showed that there was a significant difference between the morphine group and the control group (***P<0.001), indicating that naloxone administration after chronic morphine treatment can induce significant withdrawal jumping symptoms. There was a significant difference between the morphine+high-dose 3,12,13-triacetyl limaxol A group and the morphine group (*P<0.05), indicating that the withdrawal jumping symptoms induced by naloxone administration can be significantly reduced 1 hour after the morphine+3,12,13-triacetyl limaxol A (0.5 g/kg) administration.

TABLE 5

Effect of 3,12,13-triacetyl limaxol A on morphine-withdrawal jumping symptoms 3 hours after administration

| Group | Jumping times (Mean ± SEM) | % Inhibition of morphine-withdrawal jumping |
|---|---|---|
| Normal saline | 0.6 ± 0.5 | — |
| Morphine | 29.8 ± 9.5** | — |
| Morphine ± 3,12,13-triacetyl limaxol A 0.5 g/kg | 16.7 ± 4.9 | 45.0 ± 17.0 |

The results in Table 5 showed that there was a significant difference between the morphine group and the control group (***P<0.01), indicating that naloxone administration after chronic morphine treatment can induce significant withdrawal jumping symptoms. There was no significant difference between the morphine+high-dose 3,12,13-triacetyl limaxol A group and the morphine group (P>0.05), indicating that the withdrawal jumping symptoms induced by naloxone administration tended to be reduced 3 hours after the morphine+3,12,13-triacetyl limaxol A (0.5 g/kg) administration, but there was no significant difference.

4. Conclusion

The *Limax* crude extract (10 g/kg) has a significant inhibitory effect on withdrawal jumping symptoms in morphine-dependent animals 3 hours after intragastric administration, while the 3,12,13-triacetyl limaxol A (0.5 g/kg) has a significant inhibitory effect on withdrawal jumping symptoms in morphine-dependent animals 1 hour after intragastric administration, and still shows an inhibitory trend after 3 hours.

Example 11

Evaluation experiment on the sedative effect of the 3,12,13-triacetyl limaxol A (referred to as triacetyl limaxol A below)

1. Object of Experiment

This experiment aims to evaluate whether the triacetyl limaxol A has a sedative effect on mice.

2. Materials 2.1 Test Samples (1) Triacetyl limaxol A: a sample prepared in Example 3 of the present invention. To an appropriate amount of the triacetyl limaxol A was added 0.5% of Carboxymethyl cellulose sodium salt (0.5% of CMC-Na) to prepare a test sample.

(2) *Limax* crude extract: an ointment-like extract obtained by the supercritical $CO_2$ extraction in R2 in Example 3 of the present invention. To an appropriate amount of the *Limax* crude extract was added an appropriate amount of the soybean oil to prepare a test sample.

(3) U50488: commercially available from Sigma Chemical Company. To an appropriate amount of U50488 was added an appropriate amount of the normal saline to prepare 0.5 mg/ml of a control sample.

2.2 Experiment Animals

ICR mice, males, weighing 18-22 g, were commercially available from Shanghai Lingchang Biotechnology Co., Ltd.

Animal grouping: The experiment comprised a normal saline control group, a U50488 group (5 mg/kg), a triacetyl limaxol A group (500 mg/kg), and a *Limax* crude extract group (10 g/kg). Each group had 10 mice. The sedative effects of the medicines were tested 30 minutes, 60 minutes, and 120 minutes after administration.

2.3 Main Instrument:

Rotarod instrument, model JL Behv-RRTG-5, commercially available from Shanghai Jiliang Software Technology Co., Ltd.

3. Method 3.1 Dosage Design

The dose of the triacetyl limaxol A was set to 500 mg/kg, the dose of the *Limax* crude extract was set to 10 g/kg, and the dose of the control sample U50488 was set to 5 mg/kg; and the normal saline (10 ml/kg) was administered to the normal saline control group.

3.2 Dosing Regimen

Preparation of animals before administration: The animals were allowed to eat and drink freely.

Dosage determination: The dosages were calculated based on the actual weights of the animals weighed before administration.

Route of administration: The test sample was administrated orally, which was consistent with the proposed clinical route; and the control sample U50488 was administrated by intraperitoneal injection.

Frequency of administration: single dose

Volume of administration: 20 ml/kg of the test sample, and 10 ml/kg of the control sample Site of administration: The test sample was dosed by intragastric administration, and the control sample was dosed by intraperitoneal injection.

3.3 Measurement of Observation Index

Observation index: the retention time on the rotarod (s)

Measurement method: The male mice were put on the rotarod instrument with a rotarod speed set to increase evenly from 4 r/min to 40 r/min in 240 s. The retention time of the mice was used as an observation index. Two baseline measurements were determined before administration. The animals with a retention time of less than 120 s were excluded, and the animals meeting the requirements were selected for testing, with 10 in each group. The retention times of each animal 30 minutes, 60 minutes, and 120 minutes after administration were recorded. The experiment was performed for 240 s.

3.4 Statistical Analysis

The retention times of the mice in each group were represented by Mean±SEM.

A two-tailed t test was performed on the retention times in the test sample group and the normal saline control group.

4. Results

As shown in FIG. 9a to FIG. 9c (in FIG. 9a to FIG. 9c, * indicated that the p value was less than 0.05 compared with the normal saline control group, and ** indicated that the p value was less than 0.01 compared with the normal saline control group), the retention times of the animals 30 minutes after the administration of 5 mg/kg U50488 were significantly lower than that of the normal saline control group, indicating that 5 mg/kg of U50488 had a significant sedative effect, which was consistent with literature reports. The retention times of the animals 30, 60, and 120 minutes after oral administration of 500 mg/kg triacetyl limaxol A were respectively 196.7±24.3 s, 209.7±20.4 s, and 236.9±2.0 s. Compared with the normal saline control group, the retention times were not significantly reduced, indicating that 500 mg/kg of the triacetyl limaxol A did not have a significant sedative effect. In contrast, the retention times of the animals 120 minutes after oral administration of 10 g/kg Limax crude extract were significantly lower than that of the normal saline control group, indicating that the Limax crude extract had a sedative effect.

TABLE 6

Experimental data in a mouse rotarod model (Mean ± SEM) (retention time on the rotarod, s)

| Group | 30 min after administration | 60 min after administration | 120 min after administration |
|---|---|---|---|
| Normal saline control group | 204.0 ± 22.8 | 202.1 ± 24.1 | 201.9 ± 24.1 |
| U50488 group (5 mg/kg) | 100.7 ± 23.9* | 181.2 ± 1.966 | 223.7 ± 11.7 |
| Triacetyl limaxol A group (500 mg/kg) | 196.7 ± 24.3 | 209.7 ± 20.4 | 236.9 ± 2.0 |
| Limax crude extract group (10 g/kg) | 167.5 ± 25.5 | 129.6 ± 24.2 | 118.5 ± 21.9** |

*indicates that the p value is less than 0.05 compared with the normal saline control group, and **indicates that the p value is less than 0.01 compared with the normal saline control group.

5. Conclusion 500 mg/kg of the triacetyl limaxol A does not show a significant sedative effect in the mouse rotarod model 30 minutes, 60 minutes, and 120 minutes after oral administration, while 10 g/kg of the Limax crude extract shows a significant sedative effect 120 minutes after administration.

Example 12

Effect of the triacetyl limaxol A on morphine-induced conditioned place preference behavior in rats 1. Object of Experiment This experiment aims to evaluate whether a single oral administration of the triacetyl limaxol A can inhibit the morphine-induced conditioned place preference behavior in rats.

2. Materials 2.1 Test Samples (1) Triacetyl limaxol A: a sample prepared in Example 3 of the present invention.

(2) Morphine hydrochloride injection: commercially available from Shenyang No. 1 Pharmaceutical Factory of NORTHEAST PHARM.

(3) Solvent in Self-Micro emulsifying Drug Delivery System (SMEDDS) (referred to as SMEDDS solvent below): provided by Guangxi Jiufu Biotechnology Co., Ltd. and used as a stock solution, which was composed of: medium-chain triglyceride (MCT): polyoxyethylene (35) castor oil (EL): polyethylene glycol 400 (PEG-400): absolute ethanol=30:72:24:24 (by mass).

2.2 Experiment Animals

SD rats, males, weighing 180-200 g, were commercially available from SIPPR-BK Laboratory Animal Co., Ltd.

Animal grouping: The experiment comprised a normal saline control group, a normal saline+morphine group, a SMEDDS solvent+morphine group, and a triacetyl limaxol A (70 mg/kg)+morphine group. Each group had 5-7 male rats. In the experiment, the animals were orally administered, and the residence times of each animal in the left and right compartments of a box were recorded 60 minutes after administration.

2.3 Main Instrument:

Conditioned place preference (CPP) video analysis system: model JL Behv-CPPG-4, commercially available from Shanghai Jiliang Software Technology Co., Ltd.

3. Method 3.1 Dosage Design

Based on the physical dependence experiment in mice, the dose of the triacetyl limaxol A was set to 70 mg/kg, the volume of the SMEDDS solvent for intragastric administration was set to 7 ml/kg, and 7 ml/kg of the normal saline was administered intragastrically to the normal saline control group and the morphine groups.

3.2 Dosing Regimen

Preparation of animals before administration: The animals were allowed to eat and drink freely.

Dosage determination: The dosages were calculated based on the actual weights of the animals weighed before administration.

Route of administration: The test sample was administrated orally, which was consistent with the proposed clinical route.

Frequency of administration: once a day, for four consecutive days

Volume of administration: 7 ml/kg of the test sample

Site of administration: The test sample was dosed by intragastric administration.

3.3 Measurement of Observation Index

Observation index: CPP SCORE (s)=the time in the drug compartment after administration—the time in the drug compartment before administration Measurement method: After acclimation to the box, the male rats were allowed to explore the two compartments of the box for 15 minutes. According to the residence times of each animal in the left and right compartments during the exploration, the animals with a residence time of greater than 720 s or less than 180 s in any compartment were excluded. The compartment where each of the animals stayed for a short time was defined as its drug compartment. Based on the residence time in the drug compartment, the qualified animals were equally assigned to each dose group. Except for the animals in the normal saline control group, which were injected with the normal saline (1 ml/kg) subcutaneously for four consecutive days, the animals in the other three groups were subcutaneously injected with morphine (10 mg/kg) daily for four consecutive days. Immediately after the injection, the animals were put into their drug compartments to pair for 50 minutes, 2 days after the last pairing, each animal was put into the box to test for 15 minutes, 60 minutes before the testing, the normal saline was administrated intragastrically to the animals in the normal saline control group and the normal saline+morphine group, the SMEDDS solvent was administrated intragastrically to the animals in the SMEDDS solvent+morphine group, and a mixed solution of the triacetyl limaxol A and the SMEDDS solvent was administrated intragastrically to the animals in the triacetyl limaxol A+morphine group. The residence times of each animal in the left and right compartments were recorded, and the CPP SCOREs (conditioned place preference scores) were calculated. In the mixed solution of the triacetyl limaxol A and the SMEDDS solvent, the concentration of the triacetyl limaxol A was 10 mg/g. In an example, the mixed solution may be prepared by using the following method:

(1) 30.0 g of MCT, 72.0 g of EL, and 24.0 g of PEG-400 were evenly mixed;

(2) 1.5 g of the triacetyl limaxol A and 24.0 g of absolute ethanol were heated at 80° C. until the triacetyl limaxol A was completely dissolved; and (3) the solution of the triacetyl limaxol A in the absolute ethanol from step (2) was added to the mixed solution from step (1), and evenly mixed to obtained a clear solution (that is, the mixed solution of the triacetyl limaxol A and the SMEDDS solvent).

3.4 Statistical Analysis

The CPP SCOREs of the rats in each group were represented by Mean±SEM.

A two-tailed t test was performed on the CPP SCOREs of the test sample group and the normal saline control group.

4. Results

As shown in FIG. 10 (in FIG. 10, * indicated that the p value was less than 0.05 compared with the normal saline control group), the CPP SCOREs of the normal saline+ morphine group, the SMEDDS solvent+morphine group, and the triacetyl limaxol A+morphine group 60 minutes after oral administration were significantly increased compared with that of the normal saline control group, which showed a conditioned place preference behavior. Moreover, the CPP SCORE of the triacetyl limaxol A (70 mg/kg)+morphine group was 318.5±90.9 s, which was not significantly different from the normal saline+morphine group and the SMEDDS solvent+morphine group, indicating that a single oral administration of 70 mg/kg of the triacetyl limaxol A cannot affect the morphine-induced conditioned place preference behavior in rats.

TABLE 7

Effect of the triacetyl limaxol A on morphine-induced conditioned place preference behavior in rats
Experimental data CPP SCORE (Mean ± SEM) (s)

| Group | CPP SCORE (s) |
| --- | --- |
| Normal saline control group | −43.9 ± 81.9, n = 7 |
| Normal saline + morphine group | 269.8 ± 78.8*, n = 6 |
| SMEDDS solvent + morphine group | 359.6 ± 73.6*, n = 5 |
| Triacetyl limaxol A (70 mg/kg) + morphine group | 318.5 ± 90.9*, n = 7 |

*indicates that the p value is less than 0.05 compared with the normal saline control group.

5. Conclusion

A single oral administration of 70 mg/kg of the triacetyl limaxol A cannot affect the morphine-induced conditioned place preference behavior in rats.

Example 13

Effect of the concomitant administration of triacetyl limaxol A on the formation of conditioned place preference induced by morphine in rats 1. Object of Experiment This experiment aims to evaluate whether the concomitant administration of the triacetyl limaxol A can inhibit the formation of conditioned place preference induced by morphine in rats.

2. Materials 2.1 Test Samples (1) Triacetyl limaxol A: a sample prepared in Example 3 of the present invention.

(2) Morphine hydrochloride injection: commercially available from Shenyang No. 1 Pharmaceutical Factory of NORTHEAST PHARM.

(3) SMEDDS solvent: the same as that in Example 12, commercially available from Guangxi Jiufu Biotechnology Co., Ltd. and used as a stock solution.

2.2 Experiment Animals

SD rats, males, weighing 180-200 g, were commercially available from SIPPR-BK Laboratory Animal Co., Ltd.

Animal grouping: The experiment comprised a normal saline control group, a normal saline+morphine group, a SMEDDS solvent+morphine group, and a triacetyl limaxol A (70 mg/kg)+morphine group. Each group had 6-8 male rats. In the experiment, the animals were orally administered. 30 minutes after the administration, they were injected subcutaneously with morphine (10 mg/kg), and then were put into the drug compartments to pair for 50 minutes.

2.3 Main Instrument:

Conditioned place preference video analysis system: model JL Behv-CPPG-4, commercially available from Shanghai Jiliang Software Technology Co., Ltd.

3. Method 3.1 Dosage Design

Based on the physical dependence experiment in the mice, the dose of the triacetyl limaxol A was set to 70 mg/kg, the volume of the SMEDDS solvent for intragastric administration was set to 7 ml/kg, and the volume of the normal saline for intragastric administration was set to 7 ml/kg.

3.2 Dosing Regimen

Preparation of animals before administration: The animals were allowed to eat and drink freely.

Dosage determination: The dosages were calculated based on the actual weights of the animals weighed before administration.

Route of administration: The test sample was administrated orally, which was consistent with the proposed clinical route.

Frequency of administration: once a day, for four consecutive days

Volume of administration: 7 ml/kg of the test sample

Site of administration: The test sample was dosed by intragastric administration.

3.3 Measurement of Observation Index

Observation index: CPP SCORE (s)=the time in the drug compartment after administration–the time in the drug compartment before administration Measurement method: After acclimation to the box, the male rats were allowed to explore the two compartments of the box for 15 minutes. According to the residence times of each animal in the left and right compartments during the exploration, the animals with a residence time of greater than 720 s or less than 180 s in any compartment were excluded. The compartment where each of the animals stayed for a short time was defined as its drug compartment. Based on the residence time in the drug compartment, the qualified animals were equally assigned to each dose group. Except for the animals in the normal saline control group, which were injected with the normal saline (1 ml/kg) subcutaneously for four consecutive days, the animals in the other three groups were subcutaneously injected with morphine (10 mg/kg) daily for four consecutive days. Immediately after the injection, the animals were put into their drug compartments to pair for 50 minutes. 30 minutes before the injection of morphine, the normal saline was administered intragastrically to the animals in the normal saline+morphine group, the SMEDDS solvent was administered intragastrically to the animals in the SMEDDS solvent+morphine group, and a mixed solution of the triacetyl limaxol A and the SMEDDS solvent (see Example 12) was administered intragastrically to the animals in the triacetyl limaxol A (70 mg/kg)+morphine group. 2 days after the last pairing, each animal was put into the box to test for 15 minutes. The residence times of each animal in the left and right compartments were recorded, and the CPP SCOREs were calculated.

3.4 Statistical Analysis

The CPP SCOREs of the rats in each group was represented by Mean±SEM.

A two-tailed t test was performed on the CPP SCOREs of the test sample group and the normal saline control group.

4. Results

As shown in FIG. 11 (in FIG. 11, * indicated that the p value was less than 0.05 compared with the normal saline control group,  indicated that the p value was less than 0.01 compared with the normal saline control group, and * indicated that the p value was less than 0.001 compared with the normal saline control group), the CPP SCOREs of the normal saline+morphine group, the SMEDDS solvent+morphine group, and the triacetyl limaxol A+morphine group 60 minutes after oral administration were significantly increased compared with the normal saline control group, which showed a conditioned place preference behavior. Moreover, the CPP SCORE of the triacetyl limaxol A (70 mg/kg)+morphine group was 318.5±90.9 s, which was not significantly different from the normal saline+morphine group and the SMEDDS solvent+morphine group, indicating that a single oral administration of 70 mg/kg of the triacetyl limaxol A cannot affect the morphine-induced conditioned place preference behavior in rats.

TABLE 8

Effect of the triacetyl limaxol A on the formation of conditioned place preference induced by morphine in rats
Experimental data CPP SCORE (Mean ± SEM) (s)

| Group | CPP SCORE (s) |
|---|---|
| Normal saline control group | −62.0 ± 25.4, n = 7 |
| Normal saline ± morphine group | 152.2 ± 32.2***, n = 7 |
| SMEDDS solvent ± morphine group | 121.0 ± 36.6**, n = 8 |
| Triacetyl limaxol A (70 mg/kg) ± morphine group | 223.8 ± 34.0***, n = 6 |

*indicates that the p value is less than 0.05 compared with the normal saline control group, indicates that the p value is less than 0.01 compared with the normal saline control group, and *indicates that the p value is less than 0.001 compared with the normal saline control group.

5. Conclusion 70 mg/kg of the triacetyl limaxol A orally administered concomitantly with the morphine cannot affect the formation of conditioned place preference induced by morphine in rats.

Example 14

Evaluation experiment on the addictive potential of the triacetyl limaxol A

1. Object of Experiment

This experiment aims to evaluate whether the triacetyl limaxol A can induce rats to form conditioned place preference.

2. Materials 2.1 Test Samples (1) Triacetyl limaxol A (test sample): a sample prepared in Example 3 of the present invention, used as a stock solution.

(2) Morphine hydrochloride injection: commercially available from Shenyang No. 1 Pharmaceutical Factory of NORTHEAST PHARM.

(3) SMEDDS solvent: the same as that in Example 12, commercially available from Guangxi Jiufu Biotechnology Co., Ltd. and used as a stock solution.

2.2 Experiment Animals

SD rats, males, weighing 180-200 g, were commercially available from SIPPR-BK Laboratory Animal Co., Ltd.

Animal grouping: The experiment comprised a normal saline s.c group (s.c represents subcutaneous administration), a morphine group, a normal saline p.o group (p.o represents oral administration), a SMEDDS solvent control group, a 17.5 mg/kg triacetyl limaxol A group, a 35 mg/kg triacetyl limaxol A group, and a 70 mg/kg triacetyl limaxol A group. Each group had 9-12 male rats. The animals in the normal saline p.o group, the SMEDDS solvent control group, and all of the triacetyl limaxol A groups were administrated intragastrically, and 30 minutes later, they were put into the drug compartments to pair for 50 minutes, while the animals in the normal saline s.c group and the morphine group were injected subcutaneously with the normal saline and the morphine (10 mg/kg) respectively, and then immediately put into the drug compartments to pair for 50 minutes.

2.3 Main Instrument:

Conditioned place preference video analysis system: model JL Behv-CPPG-4, commercially available from Shanghai Jiliang Software Technology Co., Ltd.

3. Method 3.1 Dosage Design

Based on the physical dependence experiment in the mice, the doses of the test sample groups were set to 17.5 mg/kg, 35 mg/kg, and 70 mg/kg, and the volumes for intragastric administration were set to 7 ml/kg, and the volumes for subcutaneous injection were set to 1 ml/kg.

3.2 Dosing Regimen

Preparation of animals before administration: The animals were allowed to eat and drink freely.

Dosage determination: The dosages were calculated based on the actual weights of the animals weighed before administration.

Route of administration: The test sample was administrated orally, which was consistent with the proposed clinical route.

Frequency of administration: once a day, for four consecutive days

Volume of administration: 7 ml/kg of the test sample

Site of administration: The test sample was dosed by intragastric administration.

3.3 Measurement of Observation Index

Observation index: CPP SCORE (s)=the time in the drug compartment after administration−the time in the drug compartment before administration Measurement method: After acclimation to the box, the male rats were allowed to explore the two compartments of the box for 15 minutes. According to the residence times of each animal in the left and right compartments during the exploration, the animals with a residence time of greater than 720 s or less than 180 s in any compartment were excluded. The compartment where each of the animals stayed for a short time was defined as its drug compartment. Based on the time in the drug compartment, the qualified animals were equally assigned to each dose group. The animals in the normal saline s.c group were subcutaneously injected with the normal saline (1 ml/kg) daily for four consecutive days, and the animals in the morphine group were subcutaneously injected with morphine (10 mg/kg) daily for four consecutive days, and then the animals of the two groups were immediately put into their drug compartments to pair for 50 minutes. The animals in the normal saline p.o group were intragastrically administered with the normal saline for four consecutive days, the animals in the SMEDDS solvent control group were intragastrically administered with the SMEDDS solvent for four consecutive days, and the animals in the triacetyl limaxol A groups were intragastrically administered with the mixed solutions of the triacetyl limaxol A and the SMEDDS solvent with different doses (see Example 12) for four consecutive days. 30 minutes later, the animals of the foregoing groups were put into their drug compartments to pair for 50 minutes. 2 days after the last pairing, each animal was put into the box to test for 15 minutes. The residence times of each animal in the left and right compartments were recorded, and the CPP SCOREs were calculated.

3.4 Statistical Analysis

The CPP SCOREs of the rats in each group were represented by Mean±SEM.

A two-tailed t test was performed on the CPP SCOREs of the test sample groups and the normal saline control group.

4. Results

As shown in FIG. 12a and FIG. 12b (in the figures, * represented p<0.05 compared with the normal saline s.c group), the CPP SCORE of the morphine group after administration for four consecutive days was 208.3±16.2 s, which was significantly increased (p<0.05) compared with the normal saline s.c group (FIG. 12a), suggesting that the morphine induced conditioned place preference behavior in rats. The CPP SCOREs of the 17.5 mg/kg, 35 mg/kg, and 70 mg/kg triacetyl limaxol A groups were respectively 96.8±42.4 s, 36.4±60.5 s, and 13.4±60.6 s (Table 9), which had no significant changes compared with the SMEDDS solvent control group, indicating that different doses of the triacetyl limaxol A cannot induce the rats to form the conditioned place preference, and thus had no significant psychological dependence potential.

TABLE 9

Experimental data of CPP SCORE (Mean ± SEM) (s) for inducing the rats to form the conditioned place preference

| Group | CPP SCORE (s) |
| --- | --- |
| Normal saline s.c group | 73.0 ± 41.7, n = 10 |
| Morphine group | 208.3 ± 16.2*, n = 10 |
| Normal saline p.o group | 115.7 ± 46.8, n = 10 |
| SMEDDS solvent control group | −46.0 ± 79.2, n = 8 |
| Triacetyl limaxol A group (17.5 mg/kg) | 96.8 ± 42.4, n = 12 |
| Triacetyl limaxol A group (35 mg/kg) | 36.4 ± 60.5, n = 9 |
| Triacetyl limaxol A group (70 mg/kg) | 13.4 ± 60.6, n = 10 |

*indicates that the p value is less than 0.05 compared with the normal saline s.c group.

5. Conclusion 17.5 mg/kg, 35 mg/kg, and 70 mg/kg of the triacetyl limaxol A cannot induce the rats to form the conditioned place preference, and thus have no psychological dependence potential.

Example 15

Evaluation of the effect of the *Limax* extracts (crude extract, limaxol A, and triacetyl limaxol A) on morphine-induced physical dependence 1. Test Samples
  (1) Triacetyl limaxol A: a sample prepared in Example 3 of the present invention.
  (2) Morphine hydrochloride injection: commercially available from Shenyang No. 1 Pharmaceutical Factory of NORTHEAST PHARM.
  (3) Limaxol A: provided by Guangxi Jiufu Biotechnology Co., Ltd., having a structure of:

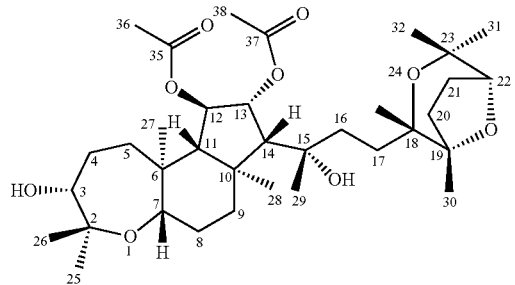

2. Experiment Animals

Kunming mice, males, weighing 18-22 g, were commercially available from the experiment animal center of Shanghai Institute of Materia Medica, Chinese Academy of Sciences.

3. Method

The animals were randomized to a normal saline control group, a morphine group, a morphine+1 g/kg triacetyl limaxol A group, and a morphine+1 g/kg limaxol A group. A mouse model of physical dependence was established by administrating morphine subcutaneously twice a day (60 mg/kg on the first day, and 80 mg/kg on the second day), with a 6-hour interval between each administration, and from day 3, administrating 100 mg/kg of morphine 7 consecutive days. On day 8, 4 mg/kg of naloxone was injected intraperitoneally 4 hours after the administration of morphine to induce withdrawal responses. 3 hours before the injection of the naloxone, the animals in each group were administrated different drugs, that is, 1 g/kg of the triacetyl limaxol A was administered to the animals in the morphine+1 g/kg triacetyl limaxol A group, and 1 g/kg of the limaxol A was administered to the animals in the morphine+1 g/kg limaxol A group, to detect the effect on the morphine-induced physical dependence symptoms.

4. Results: As Shown in Table 10

TABLE 10

| Group | Jumping times (Mean ± SEM) | Inhibition of morphine-withdrawal jumping |
|---|---|---|
| Morphine group | 38.1 ± 8.8 | — |
| Morphine ± 1 g/kg triacetyl limaxol A group | 21.7 ± 6.9 | 43.13% |
| Morphine ± 1 g/kg limaxol A group | 30.0 ± 9.7 | 21.26% |

The experimental data shows that under the same dosage conditions, the inhibition rate of the triacetyl limaxol A on the morphine-dependent mice is more than twice that of the limaxol A, and thus has a stronger biological activity and a better effect.

Example 16

Evaluation of the affinity and selectivity of triacetyllimaxol A for three subtypes of opioid receptors κ, μ, and δ

1. Object of Experiment

This experiment aims to evaluate the affinity and selectivity of triacetyllimaxol A for three subtypes of opioid receptors κ, μ, and δ.

2. Materials 2.1 Test sample: a mixed solution of triacetyllimaxol A (code name AK) and SMEDDS solvent. Preparation method: AK was mixed with SMEDDS solvent (the same as Example 12) to prepare a stock solution with a concentration of $1\times10^{-1.81}$ M, which was aliquoted into 10 μl/EP tube and preserved at −20° C. for use, and diluted to a desired concentration on the day of use.

2.2 Main Reagents 2.2.1 Membrane receptor protein: prepared by cell membranes extracted from CHO cells stably expressing receptors κ, μ, and δ which were constructed by Shanghai Institute of Materia Medica, Chinese Academy of Sciences (referring to 3.1 below);

2.2.2 Radioligands $^3$H-DAMGO (50.1 Ci/mmol, μ opioid receptor agonist), lot number 2479555;

$^3$H-DPDPE (48.6 Ci/mmol, δ opioid receptor agonist), lot number 2764670; and $^3$H-U69593 (39.1 Ci/mmol, κ opioid receptor agonist), lot number 2230633:

all of the radioligands were commercially available from PE Company.

2.2.3 Selective Ligands (Reference Ligands)

High-selective μ opioid receptor agonist DAMGO, commercially available from TOCRIS Bioscience Company, lot number 32A:

High-selective κ opioid receptor agonist (±)-trans-U50488, commercially available from TOCRIS Bioscience Company, lot number 4B/242199; and High-selective δ opioid receptor agonist SNC80, commercially available from Abcam Corporation, lot number APN11310-7-8.

2.2.4 Other Reagents

PPO (2,5-diphenyloxazole): commercially available from Sinopharm Chemical Reagent Co., Ltd, lot number 20180305;

POPOP (1,4-bis(5-phenyloxazol-2-yl)-benzene): commercially available from SigmaCorporation;

Toluene: commercially available from Sinopharm Chemical Reagent Co., Ltd. lot number 20191101;

Fetal bovine serum: commercially available from Shanghai Sunub Bio-Tech Development Inc.:

Ham's F-12: commercially available from Shanghai BasalMedia Technologies Co., LTD., lot number K120803:

G418: commercially available from Sigma Corporation:

Tris (tris(hydroxymethyl)aminomethane): commercially available from Sigma Corporation;

HEPES (N-2-Hydroxyethylpiperazine-N'-2-ethanesulfonic acid): commercially available from Amresco Inc.;

EDTA (ethylenediaminetetraacetic acid): commercially available from Invitrogen Corporation, lot number 2730C504;

EGTA (ethylene glycol-bis(2-aminoethylether)-N,N,N', N'-tetraacetic acid): commercially available from Amresco Inc.;

NaCl (sodium chloride): commercially available from Sinopharm Chemical Reagent Co., Ltd, lot number 20191031;

$MgCl_2$ (magnesium chloride): commercially available from Sinopharm Chemical Reagent Co., Ltd, lot number 20181214;

$NaH_2PO_4$ (sodium dihydrogen phosphate): commercially available from Sinopharm Chemical Reagent Co., Ltd, lot number 20140115; and Grade GF/C glass fiber filter paper: commercially available from Whatman Inc.

2.3 Main Instrument

Perkin Elmer liquid scintillation counter: model PRI-CARB 2910, commercially available from PE Company.

3. Method 3.1 Preparation of Membrane Receptor Proteins

Cells were cultured in a 10 cm² of culture dish (Ham's F-12 culture medium+10% fetal bovine serum) for several days. After the cells were grown to confluence on the culture dish, the medium was aspirated, and 3 ml of PBS/EDTA solution (0.1 M NaCl, 0.01 M $NaH_2PO_4$, and 0.04% EDTA) was added to digest for 3-5 min. The cells were completely detached by pipetting several times. The cells were collected in a 40 ml of centrifuge tube, centrifuged at 5000 rpm for 5 min, and the supernatant was discarded. Ice-cold homogenization solution (50 mM HEPES, 3 mM $MgCl_2$, and 1 mM EGTA, pH 7.4) was added to the centrifuge tube, and the solution and the precipitate obtained above were transferred to a homogenizer for homogenization. Then, the homogenate was transferred to the centrifuge tube, and centrifuged twice at 15000 rpm for 20 min to obtain a precipitate. The precipitate was homogenized by adding an appropriate amount of 50 mM Tris-HCl buffer solution, pH 7.4, to measure the protein concentration. The resulting homogenate was then aliquoted into EP tubes, and preserved in a refrigerator at −80° C. for use.

3.2 Radioligand-Receptor Binding Assay

Corresponding reagents were respectively added to flow tubes according to Table 11 to Table 13 below:

TABLE 11

Affinity profiles of κ opioid receptors

| | κ opioid membrane receptor (μg) | $^3$H-U69593 (μl) | Final concentration of U50488 (mol/L) | Final concentration of AK(mol/L) |
|---|---|---|---|---|
| Total binding tube | 50 | 10 | — | — |
| Nonspecific binding tube | 50 | 10 | $1 * 10^{-5}$ | — |
| Sample tube 1 | 50 | 10 | $1 * 10^{-4}$ | — |
| Sample tube 2 | 50 | 10 | $1 * 10^{-5}$ | — |
| Sample tube 3 | 50 | 10 | $5 * 10^{-6}$ | — |
| Sample tube 4 | 50 | 10 | $1 * 10^{-6}$ | — |
| Sample tube 5 | 50 | 10 | $1 * 10^{-7}$ | — |
| Sample tube 6 | 50 | 10 | $1 * 10^{-8}$ | — |
| Sample tube 7 | 50 | 10 | $1 * 10^{-9}$ | — |
| Sample tube 8 | 50 | 10 | $1 * 10^{-10}$ | — |
| Sample tube 9 | 50 | 10 | — | $1.537 * 10^{-3}$ |
| Sample tube 10 | 50 | 10 | — | $1.537 * 10^{-4}$ |
| Sample tube 11 | 50 | 10 | — | $1.537 * 10^{-5}$ |
| Sample tube 12 | 50 | 10 | — | $1.537 * 10^{-6}$ |
| Sample tube 13 | 50 | 10 | — | $1.537 * 10^{-7}$ |
| Sample tube 14 | 50 | 10 | — | $1.537 * 10^{-8}$ |
| Sample tube 15 | 50 | 10 | — | $1.537 * 10^{-9}$ |

Note: "—" represents no adding.

TABLE 12

Affinity profiles of δ opioid receptors

| | δ opioid membrane receptor (μg) | $^3$H-DPDPE (μl) | Final concentration of SNC80 (mol/L) | Final concentration of AK (mol/L) |
|---|---|---|---|---|
| Total binding tube | 50 | 10 | — | — |
| Nonspecific binding tube | 50 | 10 | $1 * 10^{-6}$ | — |
| Sample tube 1 | 50 | 10 | $1 * 10^{-5}$ | — |
| Sample tube 2 | 50 | 10 | $1 * 10^{-6}$ | — |
| Sample tube 3 | 50 | 10 | $1 * 10^{-7}$ | — |
| Sample tube 4 | 50 | 10 | $1 * 10^{-8}$ | — |
| Sample tube 5 | 50 | 10 | $1 * 10^{-9}$ | — |
| Sample tube 6 | 50 | 10 | $1 * 10^{-10}$ | — |
| Sample tube 7 | 50 | 10 | $1 * 10^{-11}$ | — |
| Sample tube 8 | 50 | 10 | — | $1.537 * 10^{-3}$ |
| Sample tube 9 | 50 | 10 | — | $1.537 * 10^{-4}$ |
| Sample tube 10 | 50 | 10 | — | $0.7685 * 10^{-5}$ |
| Sample tube 11 | 50 | 10 | — | $1.537 * 10^{-5}$ |
| Sample tube 12 | 50 | 10 | — | $1.537 * 10^{-6}$ |
| Sample tube 13 | 50 | 10 | — | $1.537 * 10^{-7}$ |
| Sample tube 14 | 50 | 10 | — | $1.537 * 10^{-8}$ |

Note: "—" represents no adding.

TABLE 13

Affinity profiles of μ opioid receptors

| | μ opioid membrane receptor (μg) | $^3$H-DAMGO (μl) | Final concentration of DAMGO (mol/L) | Final concentration of AK(mol/L) |
|---|---|---|---|---|
| Total binding tube | 50 | 10 | — | — |
| Nonspecific binding tube | 50 | 10 | $1 * 10^{-5}$ | — |
| Sample tube 1 | 50 | 10 | $1 * 10^{-4}$ | — |
| Sample tube 2 | 50 | 10 | $1 * 10^{-5}$ | — |
| Sample tube 3 | 50 | 10 | $1 * 10^{-6}$ | — |
| Sample tube 4 | 50 | 10 | $1 * 10^{-7}$ | — |
| Sample tube 5 | 50 | 10 | $1 * 10^{-8}$ | — |
| Sample tube 6 | 50 | 10 | $1 * 10^{-9}$ | — |
| Sample tube 7 | 50 | 10 | $1 * 10^{-10}$ | — |
| Sample tube 8 | 50 | 10 | — | $1.537 * 10^{-3}$ |
| Sample tube 9 | 50 | 10 | — | $1.537 * 10^{-4}$ |
| Sample tube 10 | 50 | 10 | — | $1.537 * 10^{-5}$ |
| Sample tube 11 | 50 | 10 | — | $1.537 * 10^{-6}$ |
| Sample tube 12 | 50 | 10 | — | $1.537 * 10^{-7}$ |
| Sample tube 13 | 50 | 10 | — | $1.537 * 10^{-8}$ |
| Sample tube 14 | 50 | 10 | — | $1.537 * 10^{-9}$ |

Note: "—" represents no adding.

The final volume of each of the foregoing tubes was 100 μl, and the tubes were incubated at 37° C. for 30 min, and finally quenched in ice water. The content of each tube was filtered under negative pressure by using GF/C glass fiber filter paper on a Millipore sample collector. The filter paper was washed with 4 ml of 50 mM Tris-HCl (pH 7.4) for three times, and dried. It was then placed in a 0.5 ml of Eppendorf tube, and 0.5 ml of lipophilic scintillation cocktail was added. Radioactive intensity was measured by using Perkin Elmer PRI-CARB 2910 liquid scintillation counter, and the inhibition rate was calculated. The experiment was repeated for more than three times in triplicate.

Inhibition rate=(total binding tube dpm−sample tube dpm)/(total binding tube dpm−nonspecific binding tube dpm)×100%.

3.3 Measurement of Protein Concentration by Using a BCA Protein Assay Kit

A 10 μl of protein standard (BSA standard protein) was diluted to a final concentration of 0.5 mg/ml. 0, 1, 2, 4, 8, 12, 16, and 20 μl of BSA standard protein and test samples (i.e., the foregoing total binding tube, the nonspecific binding tubes, and the sample tubes) were respectively added to a 96-well plate, and were added up to 20 μl with the diluted BSA standard protein. 200 μl of BCA working solution was added to each well, and incubated at 37° C. for 30 min. The absorbance at a wavelength of 562 nm was measured with a plate reader, and the protein concentration of each of the tubes was calculated according to the standard curves.

3.4 Statistical Analysis

The affinity dissociation constant $K_i$ was calculated with Prism 8.0 software, where the concentration of the labeled ligand added was 2.0 nM for $^3$H-DAMGO, 1.1 nM for $^3$H-DPDPE, and 1.5 nM for $^3$H-U69593. The dissociation constant $K_d$ was 0.93 nM for the μ receptor-ligand complex, 0.77 nM for the δ receptor-ligand complex, and 1.1 nM for the κ receptor-ligand complex.

4. Results

As shown in FIG. 13 and Table 14, AK had a high affinity for δ opioid receptor (Ki: 47.71±21.25 μM), and had low affinities for μ and κ opioid receptors.

Table 14. Affinity values (Ki) for the binding to opioid receptors in CHO cells stably expressing opioid receptors. Membranes were incubated with varying concentrations of ligands in the presence of 1.9-2.0 nM $^3$H-DAMGO, 1.0-1.1 nM $^3$H-DPDPE and 1.4-1.5 nM $^3$H-U69593. Data are expressed as the means±SEM for at least three independent experiments performed in triplicate.

TABLE 14

| Compounds | u binding affinity $K_i$ (nM) | δ binding affinity $K_i$ (nM) | κ binding affinity $K_i$ (nM) |
| --- | --- | --- | --- |
| AK | — | 4771.2 ± 2125.2 | — |
| DAMGO | 5.01 ± 0.59 | — | — |
| SNC80 | — | 10.08 ± 0.16 | — |
| U50488 | — | — | 2.19 ± 1.2 |

5. Conclusion

In vitro radioligand-receptor binding assays show that AK has a certain affinity for δ opioid receptor ($K_i$: 47.71±21.25 μM), and has no detectable affinities for μ and κ opioid receptors.

What is claimed is:

1. A method for preparing a compound having a formula:

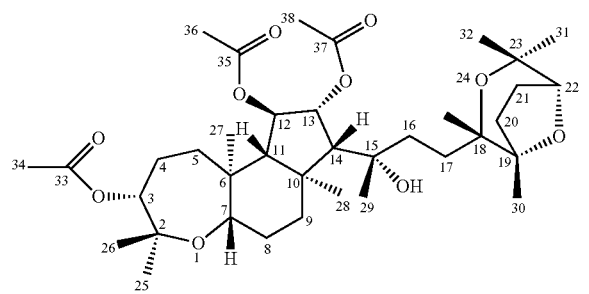

comprising the following steps:
R1: sorting *Limax*, removing impurities, and pulverizing, to obtain *Limax* powder;
R2: putting the *Limax* powder into a supercritical $CO_2$ extractor for extraction to obtain an extract;
R3: adding vegetable oil to the extract, heating and mixing evenly, cooling, standing, and filtering to obtain a precipitate, washing the precipitate with a washing solvent, and drying to obtain a dried precipitate; and
R4: adding a crystallization solvent to the dried precipitate, heating to dissolve, cooling, standing to precipitate white needle-like crystals, and filtering to obtain the crystals, recrystallizing, and drying, to obtain the compound.

2. The method for preparing the compound according to claim 1, wherein the pulverizing in R1 comprises pulverizing into 10-30 meshes.

3. The method for preparing the compound according to claim 1, wherein the conditions for the supercritical CO2 extraction in R2 comprise: pressure 20-30 kPa, temperature flow 400-500 PV, and extraction time 3-5 h.

4. The method for preparing the compound according to claim 1, wherein in R3: the vegetable oil is tea seed oil, *camellia* seed oil, soybean oil, or olive oil;
the vegetable oil is added in a weight ratio of "extract: vegetable oil=2-6:1-3";
the heating is carried out at a temperature of 60-80° C.;
the time for the standing is 7-10 days; and
the washing comprises washing with n-hexane, petroleum ether, or 120 #gasoline for 3-5 times, with an amount of 200-500 ml each time.

5. The method for preparing the compound according to claim 1, wherein in R4: the crystallization solvent is methanol, acetone, ethyl acetate, or chloroform added at an amount of 3-10 times the weight of the dried precipitate; and the time for the standing is 7-10 days.

6. A method for preparing a compound having a formula:

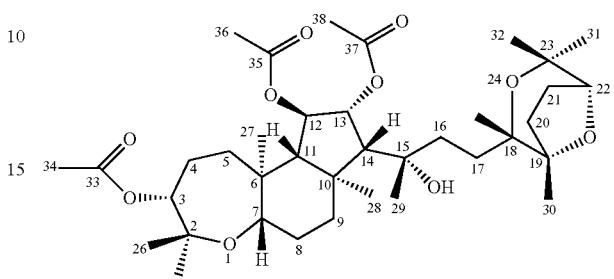

comprising the following steps:
S1: sorting *Limax*, removing impurities, and pulverizing, to obtain *Limax* powder;
S2: heating reflux extraction the *Limax* powder with a solvent, filtering, leaving a filtrate and recovering the solvent from the filtrate under reduced pressure until the recovery is complete, to obtain a thick paste;
S3: adding the thick paste to a silica gel chromatography column, eluting with an elution solvent, collecting an eluate, and recovering the elution solvent from the eluate under reduced pressure, to obtain a thick substance; and
S4: adding a dissolution solvent to the thick substance, heating to dissolve completely, cooling, and freezing to precipitate white crystals, filtering, leaving a filtrate, recovering the dissolution solvent from the filtrate under reduced pressure, and re-standing to precipitate white needle-like crystals, filtering, and drying, to obtain the crystals, recrystallizing, and drying, to obtain the compound.

7. The method for preparing the compound according to claim 6, wherein the pulverizing in S1 comprises pulverizing into 10-30 meshes.

8. The method for preparing the compound according to claim 6, wherein the solvent in S2 is one or more of ethanol, methanol, acetone, chloroform, 120#gasoline, n-hexane, petroleum ether, diethyl ether, and ethyl acetate.

9. The method for preparing the compound according to claim 6, wherein the heating reflux extraction in S2 comprises heating reflux extraction 1-3 times with the solvent, with an amount of 5-15 times the weight of the *Limax* powder each time, for 1-3 h.

10. The method for preparing the compound according to claim 6, wherein the adding to the silica gel chromatography column in S3 comprises adding silica gel to the thick paste at an amount of 4-6 times the weight of the thick paste, mixing evenly, and adding to the chromatography column pre-filled with silica gel at an amount of 2-4 times the weight of the thick paste.

11. The method for preparing the compound according to claim 6, wherein the elution solvent in S3 is methanol, acetone, or ethyl acetate, and the amount of the elution solvent used is: the volume of the elution solvent: the total weight of the silica gel in the chromatography column=1.5-3:1-2.

12. The method for preparing the compound according to claim 6, wherein the dissolution solvent in S4 is methanol or ethanol added in an amount of 4-8 times the volume of the thick substance; the freezing is carried out at a temperature of 2-10° C. for 24 hours; the recovering the solvent from the filtrate under reduced pressure comprises concentrating to of the original volume; and the time for the re-standing is 7-10 days.

13. The method for preparing the compound according to claim 6, comprising a step of pre-elution with a pre-elution solvent before the eluting with an elution solvent in S3, wherein the pre-elution solvent is petroleum ether, n-hexane, or 120#gasoline, and the amount of the pre-elution solvent used is: the volume of the pre-elution solvent: the total weight of the silica gel in the chromatography column=1-3:0.5-1.5.

* * * * *